(12) United States Patent
Suzuki et al.

(10) Patent No.: US 8,197,457 B2
(45) Date of Patent: *Jun. 12, 2012

(54) DISPOSABLE WEARING ARTICLE

(75) Inventors: Sachiyo Suzuki, Kagawa-ken (JP);
Yoshitaka Mishima, Kagawa-ken (JP)

(73) Assignee: Uni-Charm Corporation, Ehime (JP)

(*) Notice: Subject to any disclaimer, the term of this patent is extended or adjusted under 35 U.S.C. 154(b) by 934 days.

This patent is subject to a terminal disclaimer.

(21) Appl. No.: 11/302,162

(22) Filed: Dec. 14, 2005

(65) Prior Publication Data

US 2006/0135931 A1 Jun. 22, 2006

(30) Foreign Application Priority Data

Dec. 21, 2004 (JP) ................. 2004-370105

(51) Int. Cl.
  *A61F 13/15* (2006.01)
  *A61F 13/20* (2006.01)
(52) U.S. Cl. .......... 604/385.28; 604/385.27; 604/385.24
(58) Field of Classification Search ............ 604/385.08, 604/385.101, 385.24–385.3, 385.19, 348
See application file for complete search history.

(56) References Cited

U.S. PATENT DOCUMENTS

| | | | |
|---|---|---|---|
| 4,695,278 A | 9/1987 | Lawson | |
| 4,704,116 A * | 11/1987 | Enloe | 604/385.27 |
| 4,738,677 A * | 4/1988 | Foreman | 604/385.27 |
| 5,275,590 A * | 1/1994 | Huffman et al. | 604/385.27 |
| 5,554,142 A * | 9/1996 | Dreier et al. | 604/385.23 |
| 5,593,401 A * | 1/1997 | Sosalla et al. | 604/385.28 |
| 5,653,703 A * | 8/1997 | Roe et al. | 604/385.01 |
| 5,814,036 A * | 9/1998 | Ronnberg et al. | 604/385.201 |
| 6,010,490 A * | 1/2000 | Freeland et al. | 604/385.19 |
| 6,103,952 A | 8/2000 | Coles et al. | |
| 6,406,465 B1 * | 6/2002 | Otsubo | 604/385.01 |
| 6,508,798 B1 * | 1/2003 | Widlund et al. | 604/385.27 |
| 6,790,203 B2 * | 9/2004 | Een | 604/385.28 |
| 6,824,534 B2 * | 11/2004 | Mishima et al. | 604/385.01 |
| 2002/0013567 A1 * | 1/2002 | Mishima et al. | 604/385.101 |
| 2006/0135931 A1 * | 6/2006 | Suzuki et al. | 604/385.19 |
| 2006/0142727 A1 * | 6/2006 | Suzuki et al. | 604/385.19 |

FOREIGN PATENT DOCUMENTS

| | | |
|---|---|---|
| EP | 0 955 028 | 11/1999 |
| EP | 1025825 A2 * | 8/2000 |
| JP | 02-65861 | 3/1990 |
| JP | 3136654 A * | 6/1991 |
| JP | 8-322878 | 12/1996 |
| JP | 10-314222 | 12/1998 |
| TW | 330840 * | 5/1998 |
| WO | 94/28844 | 12/1994 |
| WO | 95/25493 | 9/1995 |

* cited by examiner

*Primary Examiner* — Tatyana Zalukaeva
*Assistant Examiner* — Susan Su
(74) *Attorney, Agent, or Firm* — Lowe, Hauptman, Ham & Berner, LLP

(57) ABSTRACT

A disposable wearing article has an elasticized first band lying in a front half of a crotch region and attached to distal zones of a pair of leak-barrier sheets provided on a body side of the article and an elasticized second band lying in a rear half of the crotch region and attached to the distal zones. A dimension by which distal edge segments of the distal zones extending forward from the first band in a longitudinal direction are spaced from each other is gradually enlarged from the side of the first band toward the side of a front waist region.

14 Claims, 17 Drawing Sheets

DISPOSABLE WEARING ARTICLE

RELATED APPLICATIONS

The present application is based on, and claims priority from, Japanese Application Number 2004-370105, filed Dec. 21, 2004, the disclosure of which is hereby incorporated by reference herein in its entirety.

BACKGROUND OF THE INVENTION

The present invention relates to a disposable wearing article adapted for absorption and containment of urine as well as feces.

There have already been proposed disposable diapers comprising a liquid-pervious topsheet, a liquid-impervious backsheet and a liquid-absorbent core sandwiched between these sheets so as to define, a front waist region, a rear waist region and a crotch region extending between these waist regions. The diapers further include a pair of liquid leak-barrier sheets spaced from each other by a predetermined dimension in a transverse direction and extending in the longitudinal direction and a pair of liquid-resistant partition sheets spaced from each other by a predetermined dimension in the longitudinal direction and extending in the transverse direction. For example, such a diaper is disclosed in Japanese Unexamined Patent Application Publication No. 1996-322878 (hereinafter referred to as "JP 878").

The leak-barrier sheets respectively comprise proximal zones bonded to the opposite lateral margins of the diaper and extending in the longitudinal direction, distal zones extending in the longitudinal direction in parallel to the proximal zones and normally biased to rise up above the topsheet, and fixed front and rear ends directed inward in the transverse direction and bonded to the front and rear waist regions in such a directed state. Upper edges of the respective distal zones are provided with contractible elastic members extending in the longitudinal direction. The distal zones of the respective leak-barrier sheets form barriers functioning to prevent urine and/or feces from moving sideways and thereby to prevent urine and/or feces from leaking beyond the opposite side edges of the diaper. The partition sheets are located substantially in the longitudinal middle of the crotch region, each comprising a proximal segment bonded to the topsheet and a distal segment having transversely opposite ends bonded to the distal zones of the leak-barrier sheets. Upper edges of the respective distal segments are provided with contractible elastic members extending in the transverse direction in a contractible manner. The distal segments of the respective partition sheets rise up above the topsheet as the distal zones of the respective leak-barrier sheets rise up to form barriers functioning to intercept movement of urine from the front waist region toward the rear waist region and simultaneously to intercept movement of feces from the rear waist region toward the front waist region.

In JP 878, while it may be possible for the distal zones of the respective leak-barrier sheets to prevent feces from moving sideways, these distal zones are not adapted to cover feces received by the diaper from above. This means that feces discharged in the diaper may be exposed between these leak-barrier sheets and readily come in contact with the wearer's crotch region and buttock. Consequentially, feces may cling to the wearer's crotch region and buttock and consequently, the wearer's skin may be contaminated with such feces over a wide area.

SUMMARY OF THE INVENTION

In view of the problem as has been described above, it is an object of the present invention to provide a disposable wearing article improved so that a wearer can use the article without anxiety that feces discharged in the article might cling to the wearer's inguinal region as well as buttock.

The object set forth above is achieved, according to the present invention, by an improvement in the disposable wearing article comprising: a front waist region; a rear waist region; a crotch region extending between these waist regions; a pair of transversely extending ends and a pair of longitudinally extending sides, a pair of leak-barrier sheets laid on a body-side surface of at least the crotch region among the front and rear waist regions and the crotch region. The leak-barrier sheets comprise proximal zones lying along the sides of the article so as to extend in a longitudinal direction, elasticized distal zones extending in the longitudinal direction and normally biased to rise up above the body-side surface, and fixed longitudinally ends lying on longitudinally ends of the distal zones and collapsed inward in the transverse direction.

The improvement according to the present invention comprises a first band attached to the distal zones of the leak-barrier sheets so as to extend between these distal zones in order to pull these distal zones toward each other in the transverse direction. The first band is located in the crotch region is bisected aside toward the front waist region. A dimension by which first distal edge segments of the distal zones extending forward from the first band in the longitudinal direction are spaced from each other is gradually enlarged from a side of the first band toward a side of the front waist region and a maximum dimension by which the first distal edge segments are spaced from each other is larger than a maximum dimension by which second distal edge segments of the distal zones extending rearward from the first band are spaced from each other.

With the article put on the wearer's body, the second distal edge segments of the distal zones of the respective leak-barrier sheets extending rearward from the first band in the longitudinal direction come close to or in contact with the wearer's inguinal region and further go into the wearer's buttock cleavage so as to come close to or in contact with both sides of the anus. With the article put on the wearer's body, feces discharged therein is received through a clearance defined between the second distal edge segments of the respective distal zones into the feces receiving space formed between the distal zones and the body-side surface, and the distal zones cover this feces from above. Urine discharged into a space defined between the distal zones of the respective leak-barrier sheets is absorbed and contained by the core after permeation through the body-side surface.

According to one preferred embodiment of the invention, the first band is located, assumed that a longitudinal dimension of the front half of the crotch region is bisected into a first front half placed aside toward the front waist region an a second front half placed aside toward the rear half, in the second front half.

According to another preferred embodiment of the invention, a liquid-absorbent core adapted for absorption and containment of bodily fluids is sandwiched between the body-side surface and the garment-side surface at least in the crotch region of the front and rear waist regions and the crotch region, the maximum dimension by which the first distal edge segments are spaced from each other is in a range of 26 to 120% of a minimum transverse dimension of the core extending in the crotch region and a maximum dimension by which the second distal edge segments are spaced from each other is in a range of 1 to 25% of a minimum transverse dimension of the core extending in the crotch region.

According to still another preferred embodiment of the invention, the first band is elastically stretchable and contractible in the transverse direction and contractibly attached to the distal zones of the leak-barrier sheets.

According to yet another preferred embodiment of the invention, the second band attached to the distal zones of the leak-barrier sheets so as to extend between these distal zones in order to pull these distal zones toward each other in the transverse direction and the second band is located, assumed that a longitudinal dimension of the rear half of the crotch region is bisected into a first rear half placed aside toward the front half and a second rear half placed aside toward the rear waist region, in the second rear half.

According to further another preferred embodiment of the invention, the second band is elastically stretchable and contractible in the transverse direction and contractibly attached to the distal zones of the leak-barrier sheets.

According to an additional preferred embodiment of the invention, the fixed front ends of the leak-barrier sheets are directed outward in the transverse direction and bonded to the body-side surface in such a directed state and the fixed rear ends of the leak-barrier sheets are directed inward in the transverse direction and bonded to the body-side surface in such a directed state.

According to an another additional preferred embodiment of the invention, a dimension by which the second distal edge segments of the distal zones are spaced from each other is gradually reduced from the side of the first band toward the side of the rear waist region.

In the disposable wearing article according to the present invention, the feces receiving space is formed between the distal zones and the body-side surface behind the first band so that feces discharged in the article is received in this feces receiving space through the clearance defined between the second distal edge segments of the respective distal zones extending rearward from the first band in the longitudinal direction. The distal zones of the respective leak-barrier sheets extending rearward from the first band cover feces received in the feces receiving space from above and thereby confine feces within the feces receiving space. Consequentially, it is not apprehended that feces might be exposed between the leak-barrier sheets and cling to the wearer's crotch region and buttock. In this way, the wearer's skin is protected from soil with feces. In this article, the dimension by which the first distal edge segments of the distal zones of the respective leak-barrier sheets is gradually enlarged from a side of the first band toward a side of the front waist region so that the distal zones of the leak-barrier sheets reliably prevent urine discharged in the article from moving sideways and leaking beyond the side margins of the article.

In the case of the wearing article having the first band laid in the second front half of the crotch region assumed to be bisected into the first and second front halves, the segments of the distal zones of the leak-barrier sheets extending rearward from the first band in the longitudinal direction effectively cover feces from above to confine feces within the feces receiving space. Thus there is no anxiety that the feces might be exposed between the leak-barrier sheets and cling to the wearer's crotch region and buttock. In this way, the wearer's skin is protected from soil with feces. In the first front half of the crotch region, the distal zones of the respective leak-barrier sheets prevent the urine discharged in the article from moving sideways and leaking beyond the side margins of the article.

In the wearing article implemented so that a maximum dimension by which the first distal edge segments are spaced from each other is in a range of 26 to 120% of a minimum transverse dimension of the core extending in the crotch region and a maximum dimension by which the second distal edge segments are spaced from each other is in a range of 1 to 25% of a minimum transverse dimension of the core, the distal zones of the respective leak-barrier sheets reliably cover feces discharged in the article from above to prevent feces might be exposed between the leak-barrier sheets and contaminate the wearer's skin. In this article, the distal zones of the respective leak-barrier sheets extending forward from the first band in the longitudinal direction prevent the urine discharged in the article from moving sideways and leaking beyond the side margins of the article.

In the wearing article implemented so that the first band is elastically stretchable and contractible in the transverse direction and contractibly attached to the distal zones of the respective leak-barrier sheets, even if movement of the wearer tends to move the distal zones of the respective leak-barrier sheets sideways, the contractile force of the first band functions to hold the second distal edge segments of the distal zones around the transverse middle of the crotch region. Thus, movement of the distal zones is restrained by the contractile force of the first band so that the distal zones do not significantly move and the second distal edge segments of the distal zones are maintained close to or in contact with the wearer's inguinal region and both sides of the anus. With this article put on the wearer's body, the distal zones of the respective leak-barrier extending rearward from the first band in the longitudinal direction are maintained substantially at the predetermined relative positions and feces discharged in the article reliably are received in the feces receiving space through the second distal edge segments of the distal zones.

With the wearing article put on the wearer's article provided in the second rear half of the crotch region with the second band functioning to pull the distal zones of the respective leak-barrier sheets closer to each other, this second band restrains movement of the segments of the distal zones of the respective leak-barrier sheets extending rearward from the first band in the longitudinal direction. Specifically, even if movement of the wearer is transmitted to the these distal zones, the distal zones are not significantly moved from the positions at which the second distal edge segments of the distal zones are maintained closer to or in contact with the wearer's inguinal region and both sides of the anus. With this article put on the wearer's body, the segments of the distal zones of the respective leak-barrier sheets extending rearward from the first band in the longitudinal direction are not moved from the desired positions and therefore it is ensured that feces discharged in the article is received in the feces receiving space through the clearance defined between the second distal edge segments of the distal zones.

In the wearing article implemented so that the second band is elastically stretchable and contractible in the transverse direction and contractibly attached to the distal zones of the respective leak-barrier sheets, even if the distal zones of the respective leak-barrier sheets tend to move sideways due to movement of the wearer, a contractile force of the second band functions to maintain the second distal edge segments of the distal zones around the transverse middle of the crotch region. In this way, a contractile force of the second band restrains movement of the distal zones so that the second distal edge segments of these distal zones may be substantially maintained closer to or in contact with the wearer's inguinal region and both side of the anus. With this article put on the wearer's body, the segments of the distal zones of the respective leak-barrier sheets extending rearward from the first band in the longitudinal direction are substantially immobile and consequentially feces discharged in the article is reliably received in the feces receiving space through the clearance defined between the second distal edge segments of the distal zones.

The same effect is achieved also by the wearing article implemented so that the fixed front ends of the respective leak-barrier sheets are directed outward in the transverse direction and bonded to the body-side surface in such a directed state while the fixed rear ends of the respective leak-barrier sheets are directed inward in the transverse direction and bonded to the body-side surface in such a directed state. Specifically, this unique arrangement allows the dimension by that the first distal edge segments of the distal zones of the respective leak-barrier sheets are spaced from each other to be gradually enlarged from the side of the first band toward the side of the front waist region and thereby eliminates an anxiety that discharge of urine might occur outside the distal zones of the respective leak-barrier sheets. In addition, these distal zones prevent the discharged urine from moving sideways and leaking beyond the side margins of the article.

With the wearing article exploited in the manner that the dimension by which the second distal edge segments of the distal zones spaced from each other is gradually reduced from the side of the first band toward the side of the rear waist region, the distal zones of the respective leak-barrier sheets extending rearward from the first band in the longitudinal direction reliably cover the feces discharged in the article from above and thereby confine feces within the feces receiving space. In this way, there is no possibility that feces discharged in the article might be exposed between the leak-barrier sheets and cling to the wearer's crotch region and buttock. Thus the wearer's skin is reliably protected from soil with feces.

DETAILED DESCRIPTION OF THE PREFERRED EMBODIMENTS

Details of a disposable wearing article according to the present invention will be more fully understood from the description given hereunder with reference to the accompanying drawings.

Figure 1:
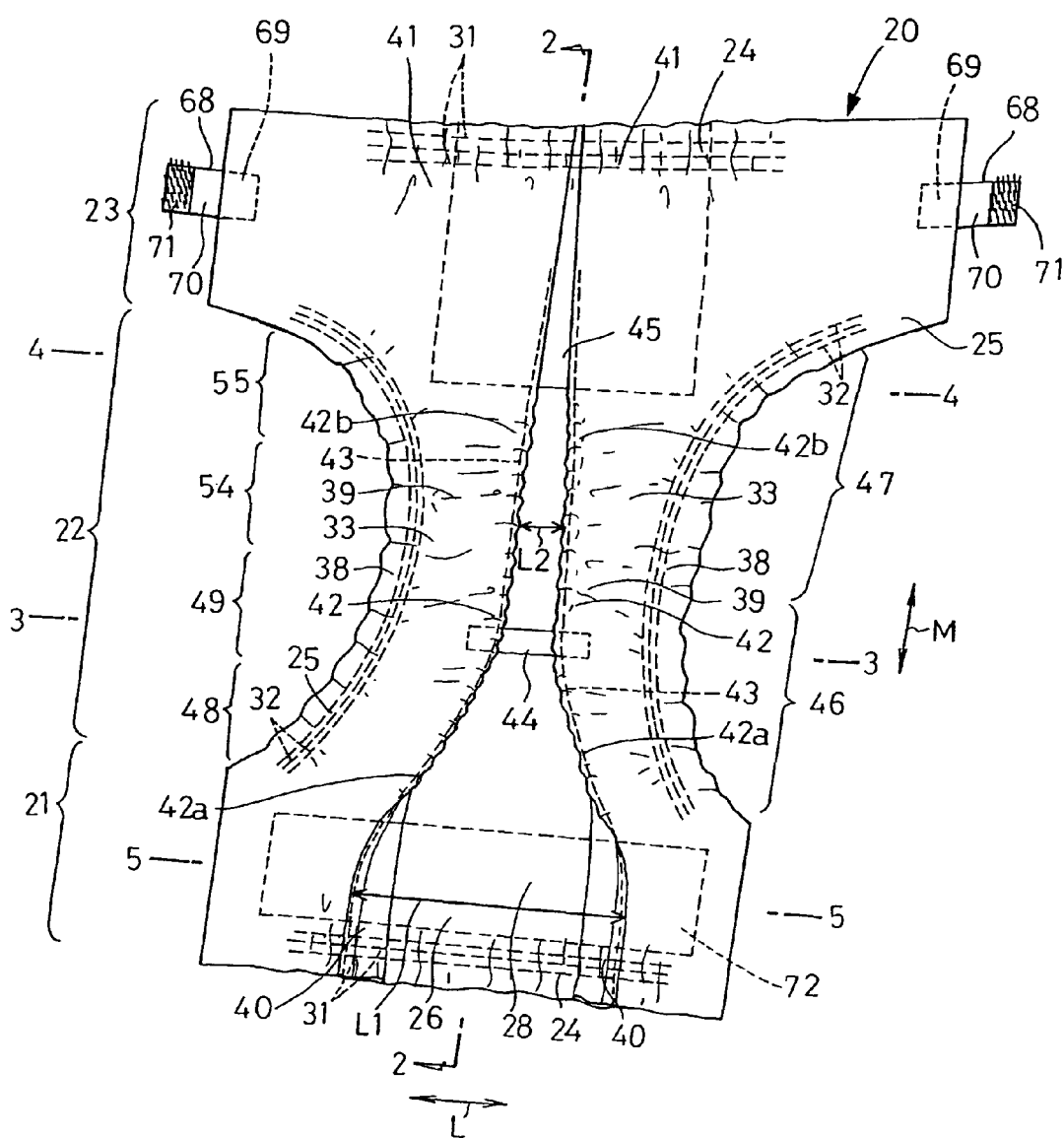
FIG. 1 is a perspective view showing a first embodiment of a wearing article according to the invention.
Figure 2:
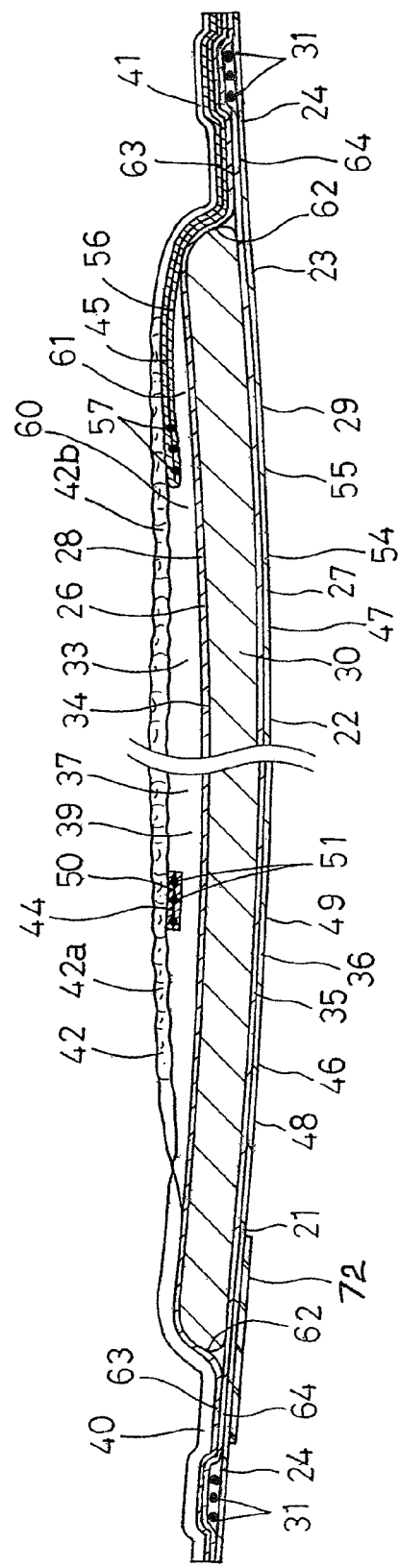
FIG. 2 is a sectional view taken along the line 2-2 in FIG. 1 with a crotch region partially cutaway.
Figure 3:
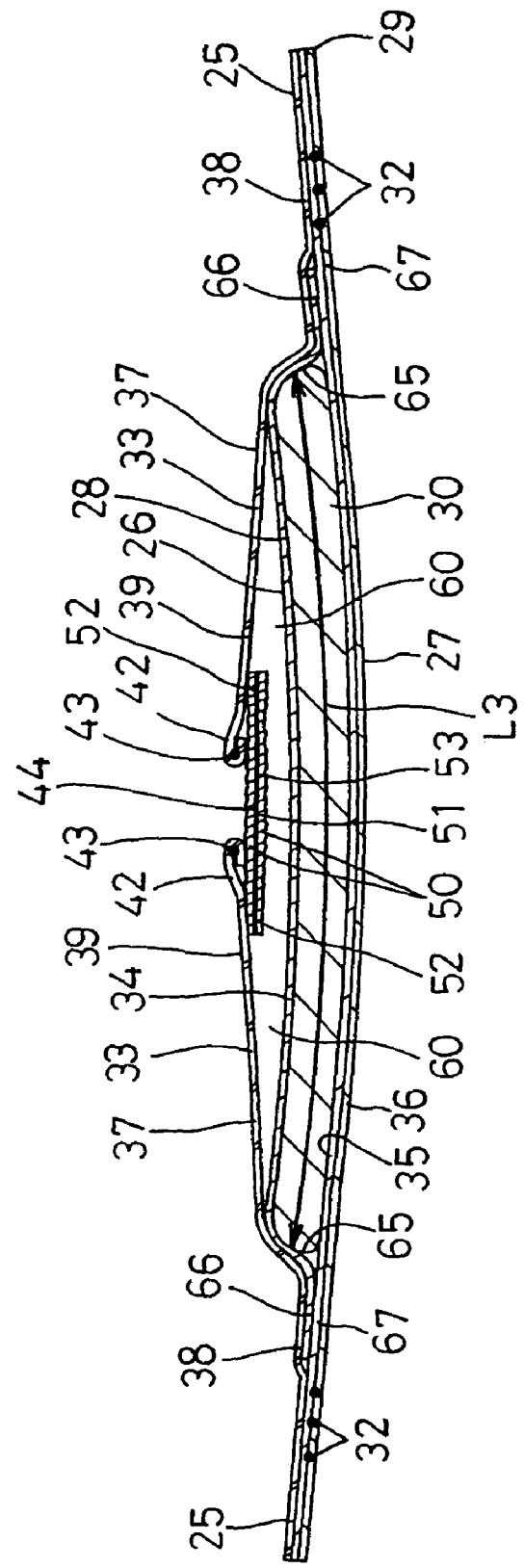
FIG. 3 is a sectional view taken along the line 3-3 in FIG. 1.
Figure 4:
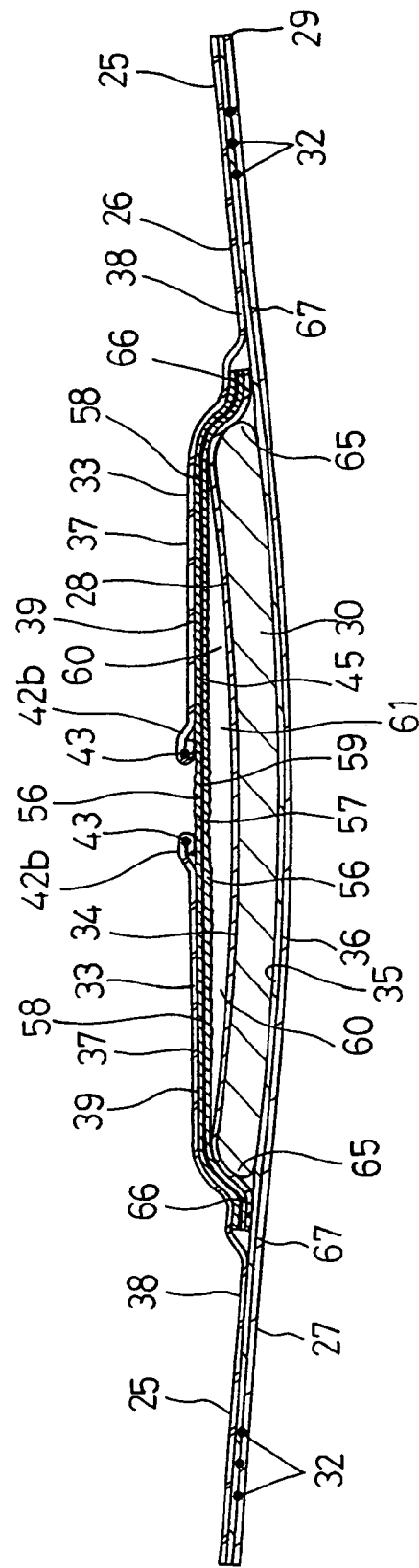
FIG. 4 is a sectional view taken along the line 4-4 in FIG. 1.
Figure 5:
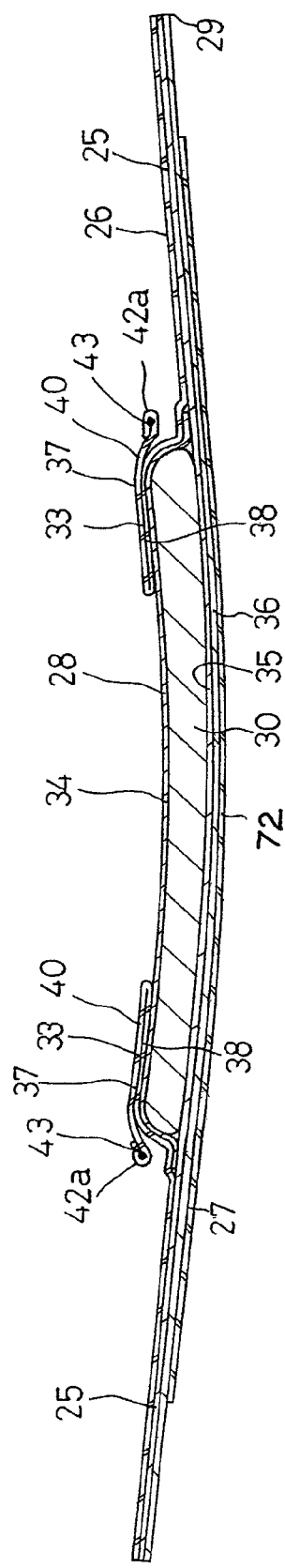
FIG. 5 is a sectional view taken along the line 5-5 in FIG. 1.

FIG. 1 is a perspective view showing a wearing article according to a first embodiment of the invention, FIG. 2 is a sectional view taken along the line 2-2 in FIG. 1 with a crotch region partially cutaway, FIG. 3 is a sectional view taken along the line 3-3 in FIG. 1 and FIG. 4 is a sectional view taken along the line 4-4 in FIG. 1. FIG. 5 is a sectional view taken along the line 5-5 in FIG. 1. In FIG. 1, a transverse direction is indicated by an arrow L and a longitudinal direction is indicated by an arrow M.

An article 20 has, as viewed in the longitudinal direction, a front waist region 21, a rear waist region 23 and a crotch region 22 extending between these waist regions 21, 23. The article 20 is contoured by transversely extending front and rear ends 24 and longitudinally extending side margins 25 between the front and rear ends 24. The article 20 has a body-side surface 26 destined to come in contact with the wearer's body and a garment-side surface 27 destined to face away from the wearer's body. The article 20 comprises a liquid-pervious topsheet 28 defining the body-side surface 26, a liquid-impervious backsheet 29 defining the garment-side surface 27 and a liquid-absorbent core 30 sandwiched between these sheets 28, 29 so as to extend over the front waist region 21, the crotch region 22 and the rear waist region 23. The side margins 25 of the crotch region 22 describe circular arcs which are convex inward in the transverse direction. Thus, the article 20 has a generally an hourglass planar shape as will be apparent from FIG. 1. This article 20 is of so-called open-type having the front and rear waist regions 21, 23 not connected with each other until the article 20 is put on the wearer's body.

A plurality of waist elastic members 31 extending in the transverse direction are contractibly attached to the transversely extending ends 24, respectively. A plurality of leg elastic members 32 extending in the longitudinal direction are contractibly attached to the longitudinally side margins 25. The side margins 25 are provided also with a pair of leak-barrier sheets 33 opposed to and spaced from each other in the transverse direction and extending between the front and rear waist regions 21, 23. As a stock material for the topsheet 28, hydrophilic fibrous nonwoven fabric 34 is used. As stock material for the backsheet 29, a composite nonwoven fabric composed of two hydrophobic fibrous nonwoven fabric layers 35, 36 laminated together. The core 30 comprises a mixture of particulate or fibrous super-absorbent polymer and fluff pulp or a mixture of particulate or fibrous super-absorbent polymer, fluff pulp and thermoplastic synthetic resin fiber, in any case, compressed to a desired thickness. Consequentially, the core 30 has a stiffness higher than those of the top- and backsheets 28, 29. The core 30 is covered in its entirety with a tissue paper (not shown) in order to prevent the core 30 from getting out of its initial shape and/or to prevent the polymers from partially falling off. The core 30 is bonded by the intermediary of the tissue paper to respective inner surfaces of the top- and backsheets 28, 29. The polymer may be selected from the group consisting of starch- or cellulose-based polymer or synthetic polymer. In the article 20, an outer surface of the topsheet 28 and an outer surface of the leak-barrier sheets 33 define the body-side surface 26 while an outer surface of the backsheet 29 defines the garment-side surface 27.

As stock material for the leak-barrier sheets 33, a hydrophobic fibrous nonwoven fabric 37 is used. Each of the leak-barrier sheets 33 comprises a proximal zone 38 lying on each of the side margins 25 and extending in the longitudinal direction, an elasticized distal zone 39 extending generally in the longitudinal direction and normally biased to rise up above the topsheet 28, and fixed front and rear ends 40, 41 lying on longitudinal ends of the distal zone 39. Elastic members 43 extending in the longitudinal direction are contractibly attached to distal edges 42 of the respective distal zones 39. More specifically, these elastic members 43 are stretched at a predetermined ratio in the longitudinal direction and bonded in such a stretched state to the respective distal zones 39. The fixed front end 40 is directed outward in the transverse direction of the article 20 while the fixed rear end 41 is directed inward in the transverse direction of the article 20. The leak-barrier sheets 33 are provided with an elongate first band 44 and a rectangular second band 45 both contractibly attached to the leak-barrier sheets 33 and serving to pull the distal zones 39, 39 closer to each other. In the leak-barrier sheets 33, the elastic members 43 contract as the article 20 bows with the body-side surface 26 inside and thereby cause the distal zones 39 to rise up above the outer surface of the topsheet 28. In this way, the distal zones 39 form barriers preventing urine and/or feces from moving sideways.

The first band 44 is interposed between the distal zones 39 of the respective leak-barrier sheets 33 spaced from and opposed to each other and extends in the transverse direction. A location of this first band 44 may be strictly defined as follows: Assumed that a longitudinal dimension of the crotch region 22 is bisected into a front half 46 placed aside toward the front waist region 21 and a rear half 47 placed aside toward the rear waist region 23, the first band 44 lies in the front half 46. More strictly, assumed that a longitudinal dimension of the front half 46 is bisected into a first front half 48 placed aside toward the front waist region 21 and a second front half 49 placed aside toward the rear half 47, the first band 44 lies in this second front half 49. In other words, on the assumption that the longitudinal dimension of the crotch region 22 is divided equally into four zones comprising a first zone (corresponding to the first front half 48) through a fourth zone (corresponding to a second rear half 55 as will be described later) arranged from the side of the front waist region 21 toward the rear waist region 23, the first band 44 lies in the second zone (corresponding to the second front half 49).

The first band 44 comprises a hydrophobic or hydrophilic fibrous nonwoven fabric 50 and a plurality of elastic members 51 contractibly attached to this nonwoven fabric 50. The elastic members 51 extend in the transverse direction between the distal zones 39 opposed to each other. The elastic members 51 are stretched at a predetermined ratio in the transverse direction and bonded in such a stretched state to the nonwoven fabric 50. Therefore, the first band 44 is elastically stretchable and contractible in the transverse direction. The first band 44 has fixed ends 52 bonded to the respective distal zones 39 in the vicinity of the distal edges 42 thereof and intermediate segment 53 extending between the fixed ends 52 and left free from the topsheet 28 as well as from the leak-barrier sheets 33. The fixed ends 52 are bonded to the respective distal zones 39 while the first band 44 is stretched at a predetermined ratio in the transverse direction.

The second band 45 extends between the distal zones 39 opposed to each other and further extends between the fixed rear ends 41. More strictly, assumed that a longitudinal dimension of the rear half 47 of the crotch region 22 is bisected into a first rear half 54 placed aside toward the front half 46 and a second rear half 55 placed aside toward the rear waist region 23, the second band 45 lies in this second rear half 55. In other words, on the assumption that the longitudinal dimension of the crotch region 22 is divided equally into four zones comprising the first zone (corresponding to the first front half 48) through the fourth zone (corresponding to the second rear half 55) arranged from the side of the front waist region 21 toward the side of the rear waist region 23, the second band 45 lies in the fourth zone (corresponding to the second rear half 55).

The second band 45 comprises a hydrophobic or hydrophilic fibrous nonwoven fabric 56 and a plurality of elastic members 57 contractibly attached to the nonwoven fabric 56. The elastic members 57 extend in the transverse direction between the distal zones 39 opposed to each other. The elastic members 57 are stretched at a predetermined ratio in the transverse direction and bonded in such a stretched state to the nonwoven fabric 56. Therefore, the zone of this second band 45 defined between the distal zones 39 is elastically stretchable and contractible in the transverse direction. The second band 45 has fixed transverse ends 58 bonded to the respective proximal zones 38 as well as to the respective distal zones 39 and intermediate segment 59 extending between the fixed transversely ends 58 and left free from the topsheet 28 as well as from the leak-barrier sheets 33. The fixed transverse ends 58 are bonded to the respective distal zones 39 while the second band 45 is stretched at a predetermined ratio in the transverse direction. A zone of the second band 45 extending between the respective fixed rear ends 41 is bonded to the outer surface of the topsheet 28 and to the inner surfaces of the respective leak-barrier sheets 33.

Opposite distal edge segments 42a (i.e., first distal edge segments) of the respective distal zones 39 extending forward from the first band 44 in the longitudinal direction are spaced from each other in the transverse direction by a dimension which is gradually enlarged from the side of the first band 44 toward the side of the front waist region 21. Opposite distal edge segments 42b (i.e., second distal edge segments) of the respective distal zones 39 extending rearward from the first band 44 in the longitudinal direction are spaced from each other in the transverse direction by a dimension which is gradually reduced from the side of the first band 44 toward the side of the rear waist region 23. Feces receiving space 60 is formed between the segments of the distal zones 39 extending rearward from the first band 44 in the longitudinal direction and the topsheet 28. Between the topsheet 28 and the second band 45, a pocket 61 is formed, which opens from the rear waist region 23 toward a middle of the crotch region 22 as viewed in the longitudinal direction.

The longitudinal ends 24 respectively comprise respective ends 63, 64 of the top- and backsheets 28, 29 extending outward from longitudinal ends 62 of the core 30 and the longitudinal ends 40, 41 of the respective leak-barrier sheets 33. The ends 24, 63, 64 are overlapped together and have respective inner surfaces bonded together. The fixed front ends 40 of the respective leak-barrier sheets 33 are laid in the front waist region 21 and bonded to the respective proximal zones 38 in a transversely outward directed state. The fixed rear ends 41 of the respective leak-barrier sheets 33 are laid in the rear waist region 23 and bonded to the outer surface of the second band 45 in a transversely inward directed state. The waist elastic members 31 are sandwiched between the nonwoven fabric layers 35, 36 forming the backsheet 29, stretched at a predetermined ratio in the transverse direction and bonded to these nonwoven fabric layers 35, 36 in such a stretched state.

The side margins 25 respectively comprise respective side margins 66, 67 of the top- and backsheets 28, 29 extending transversely outward from side edges 65 of the core 30 and the proximal zones 38 of the respective leak-barrier sheets 33. Along the side margins 25, the side margins 66 of the topsheet 28 extend transversely outward slightly beyond the respective side edges 65 of the core 30 and the respective side margins 67 of the backsheet 29 as well as the proximal zones 38 of the respective leak-barrier sheets 33 extend further transversely outward beyond the side margins 66. Along the side margins 25, the side margins 66, 67 of the top- and backsheets 28, 29 are overlapped together with the proximal zones 38 of the respective leak-barrier sheets 33, the top- and backsheets 28, 29 have respective inner surfaces bonded to each other, and outer and inner surfaces of the top- and backsheets 28, 29, respectively, are bonded to the inner surfaces of the respective leak-barrier sheets 33. The leg elastic members 32 are sandwiched between the nonwoven fabric layers 35, 36 forming together the backsheet 29, stretched at a predetermined ratio in the longitudinal direction and bonded to these nonwoven fabric layers 35, 36 in such a stretched state.

Tape fasteners 68 made of a plastic sheet are attached to the side margins 25 of the rear waist region 23. Each of the tape fasteners 68 has a fixed section 69 and a free section 70 both extending in the transverse direction. The fixed section 69 is sandwiched between the side margin 67 of the backsheet 29 and the proximal zone 38 of the leak-barrier sheet 33 and bonded to the respective inner surface of these sheets 29, 33. A male mechanical fastener 71 having a plurality of hooks is attached to the inner surface of the free section 70. Alternatively, the inner surface of the free section 70 may be coated with a pressure-sensitive adhesive instead of attaching thereto the male mechanical fastener 71.

The front waist region 21 is provided with a target tape 72 on which the free section 70 of the tape fastener 68 is detachably anchored. The target tape 72 takes the form of a female mechanical fastener 73 comprising a plastic base sheet and a plurality of loops protruding from the plastic base sheet. The target tape 72 is permanently bonded to the outer surface of the backsheet 29. When the free section 70 of the tape fastener 68 is coated with a pressure-sensitive adhesive, a plastic film may be used as the target tape 72.

Figure 6:
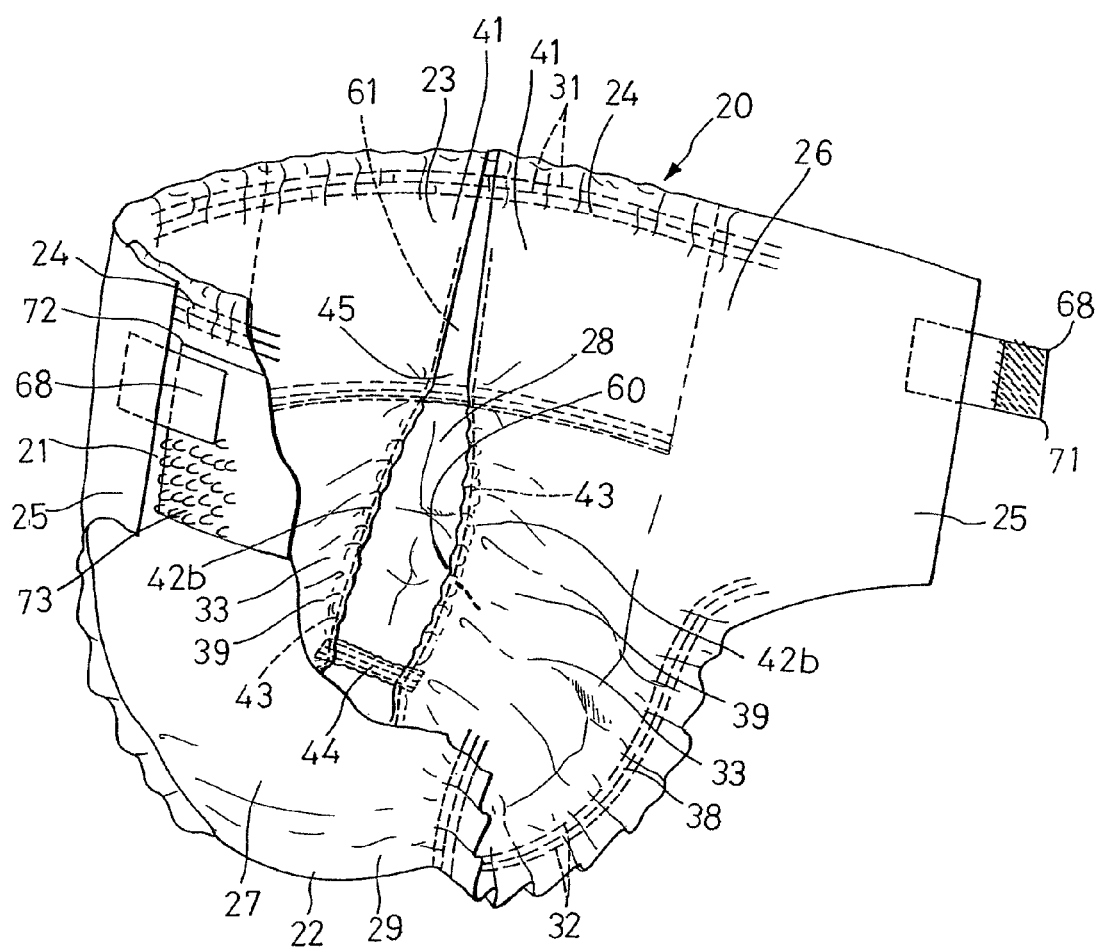
FIG. 6 is a partially cutaway perspective view showing the article in the course of being put on the wearer's body as viewed from the side of the front waist region.
Figure 7:
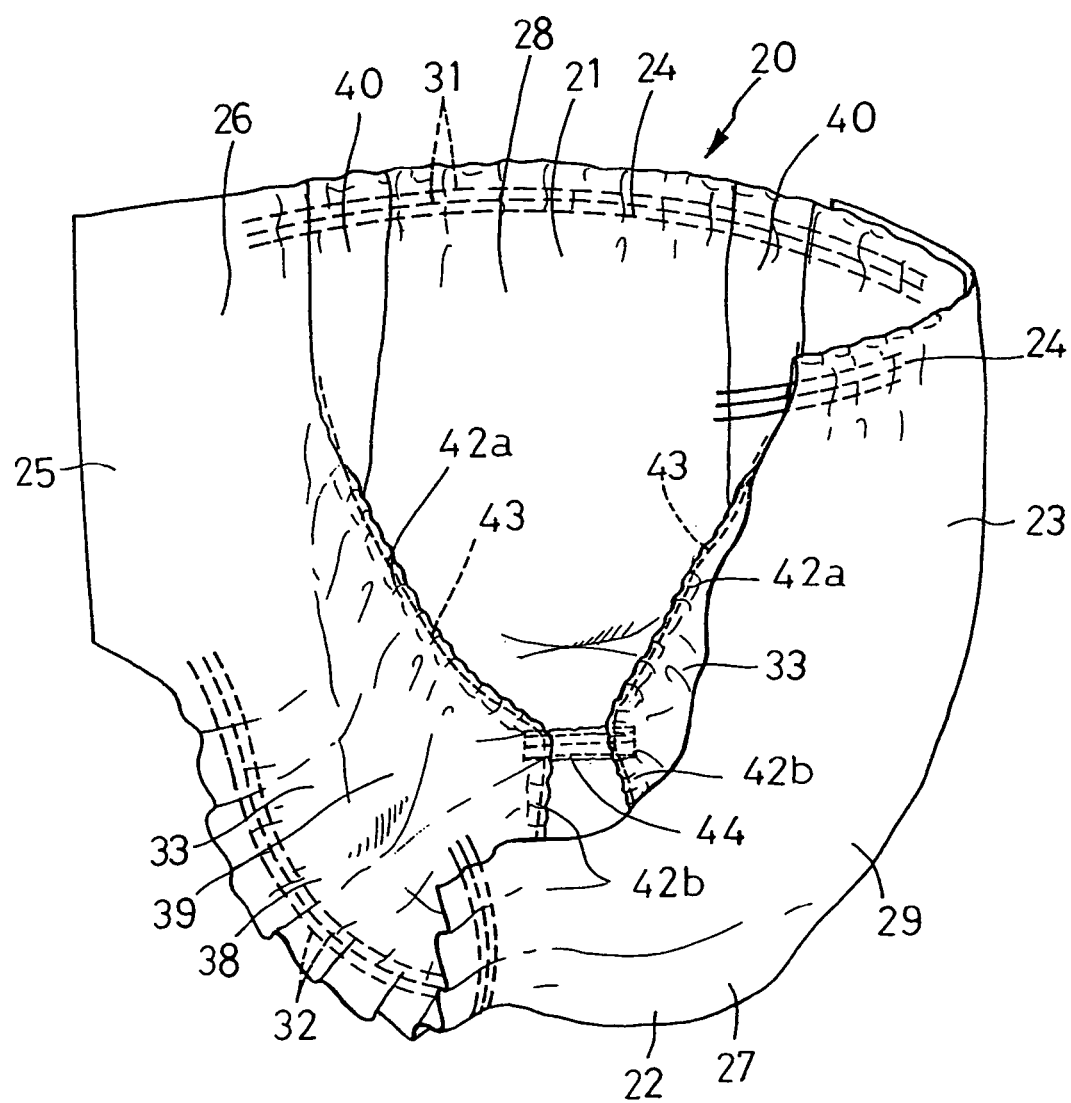
FIG. 7 is a partially cutaway perspective view showing the article in the course of being put on the wearer's body as viewed from the side of the rear waist region.
Figure 8:
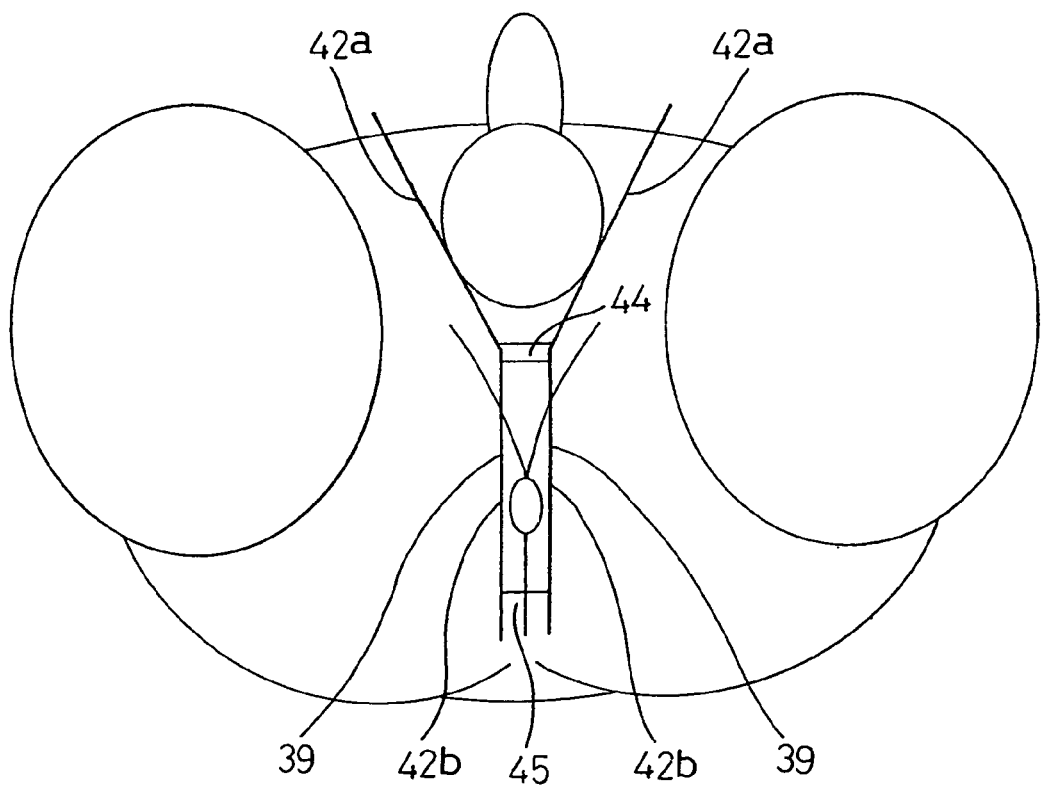
FIG. 8 is a schematic diagram illustrating positions to which upper edges of respective distal zones move as the article is put on the wearer's body.
Figure 9:
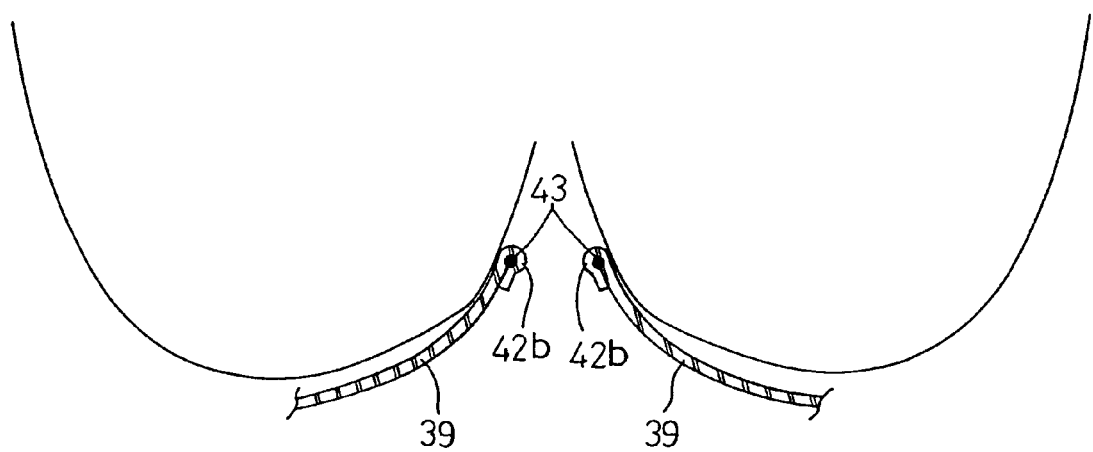
FIG. 9 is a schematic diagram illustrating positions to which the upper edges of the respective distal zones move as the article is put on the wearer's body.

FIG. 6 is a partially cutaway perspective view showing the article 20 in the course of being put on the wearer's body as viewed from the side of the front waist region 21 and FIG. 7 is a partially cutaway perspective view showing the article 20 in the course of being put on the wearer's body as viewed from the side of the rear waist region 23. FIGS. 8 and 9 are schematic diagrams illustrating positions of the distal edge segments 42a, 42b of the respective distal zones 39 in the article 20 put on the wearer's body, respectively. Specifically, FIG. 8 illustrates the wearer's crotch region as viewed from below and FIG. 9 illustrates the wearer as viewed from the side of the buttock. The article 20 may be put on the wearer's body in accordance with, for example, the steps of a procedure as follow: The wearer's buttock is placed on the bodyside surface 26 of the crotch region 22 which is, in turn, folded onto the wearer's abdominal region. Then the side margins 25 of the rear waist region 23 are folded toward the wearer's abdominal region and placed on the respective outer sides of the side margins 25 of the front waist region 21. Thereupon, the free sections 70 of the respective tape fasteners 68 are anchored on the target tape 72 to connect the rear waist region 23 with the front waist region 21. A waist-hole and a pair of leg-holes are formed (not shown) as the front and rear waist regions 21, 23 are connected with each other in this manner.

With the article 20 put on the wearer's body, the distal edge segments 42b of the distal zones 39 of the respective leak-barrier sheets 33 extending rearward from the first band 44 in the longitudinal direction come close to or in contact with the wearer's inguinal region and further go into the wearer's buttock cleavage so as to come close to or in contact with both sides of the anus. With the article 20 put on the wearer's body, feces discharged therein is received through a clearance defined between the distal edge segments 42b of the respective distal zones 39 into the feces receiving space 60 and the pocket 61. Feces received in this manner are covered from above with the distal zones 39 and the intermediate segment 59 of the second band 45. Urine discharged into a space defined between the distal edge segments 42a of the respective distal zones 39 is absorbed and contained by the core 30 permeating through the topsheet 28.

With the article 20 put on the wearer's body, the distal edge segments 42b of the distal zones 39 of the respective leak-barrier sheets 33 extending rearward from the first band 44 cooperate with the intermediate segment 59 of the second band 45 to cover feces reliably from above to confine feces within the feces receiving space 60 and the pocket 61 because the dimension by which the distal edge segments 42b of the respective distal zones 39 are spaced from each other is gradually reduced from the side of the first band 44 toward the side of the rear waist region 23. With the article 20 put on the wearer's body, it is not apprehended that feces once received into the feces receiving space 60 and the pocket 61 might be exposed between the distal zones 39 and come in contact with the wearer's crotch region and/or buttock. Consequentially, the wearer's crotch region and buttock are protected against any amount of feces possibly clinging thereto and thus the wearer's skin is protected against soil with feces. The article 20 allows the distal zones 39 of the respective leak-barrier sheets 33 to prevent urine as well as feces from moving sideways and thereby to prevent urine as well as feces from leaking beyond the side margins 25. At the same time, movement of feces in the longitudinal direction is intercepted by the intermediate segment 59 of the second band 45. In this way, there is no anxiety that any amount of feces discharged in the article 20 might leak from the rear waist region 23.

In the article 20, the first and second bands 44, 45 both having elasticity in the transverse direction are contractibly attached to the distal zones 39 of the respective leak-barrier sheets 33. Even if movement of the wearer biases the distal zones 39 to move in the transverse direction, a contractile force of the first and second bands 44, 45 functions to hold the distal edge segments 42b around the transverse middle of the crotch region 22 and thereby to restrain movement of the distal zones 39. With the article 20 put on the wearer's body, it is thus ensured that the segments of the distal zones 39 of the respective leak-barrier sheets 33 extending rearward in the longitudinal direction from the first band 44 do not significantly shift away from the predetermined positions. In other words, the distal edge segments 42b of the distal zones 39 are maintained close to or in contact with the inguinal region as well as both sides of the anus of the wearer. In this way, it is ensured that feces discharged in the article 20 is reliably received by the feces receiving space 60 and the pocket 61 through the clearance defined between the distal edge segments 42b.

In the article 20, the maximum dimension L1 by which the distal edge segments 42a of the respective distal zones 39 are spaced from each other is larger than the maximum dimension L2 by which the distal edge segments 42b of the distal zones 39 are spaced from each other. An area of the outer surface (i.e., body-side surface 26) of the topsheet 28 exposed between the distal edge segments 42a is correspondingly larger than an area of the outer surface (i.e., body-side surface 26) of the topsheet 28 exposed between the distal edge segments 42b. More specifically, the maximum dimension L1 by which the distal edge segments 42a are spaced from each other is in a range of 26 to 120%, preferably 50 to 120%, more preferably 75 to 110% of the minimum transverse dimension L3 between the side edges 65 of the core 30 extending in the crotch region 22. If the maximum dimension L1 by which the distal edge segments 42a are spaced from each other is less than 26% of the minimum transverse dimension L3 of the core 30, the dimension by which the distal edge segments 42a are spaced from each other will be insufficient and discharge of urine may occur outside the respective distal zones 39.

In the article 20, the maximum dimension L2 by which the distal edge segments 42b of the respective distal zones 39 is in a range of 1 to 25%, preferably 4 to 20% of the minimum transverse dimension L3 between the side edges 65 of the core 30. If the maximum dimension L2 by which the distal edge segments 42b are spaced from each other exceeds 25% of the minimum transverse dimension L3 of the core 30, it may be impossible for the distal zones 39 to cover feces effectively from above. Consequentially feces may be exposed between the distal zones 39 and the wearer's skin may be soiled over a large area including the crotch region and the buttock with feces clinging thereto. If the maximum dimension L2 by which the distal edge segments 42b are spaced from each other is less than 1% of the minimum transverse dimension L3 of the core 30, it may be difficult for feces to pass through the clearance defined between the distal edge segments 42b and discharge of feces may occur outside the distal zones 39.

So far as the article 20 for baby is concerned, the minimum transverse dimension L3 of the core 30 extending in the crotch region 22 is in a range of about 5 cm to about 9 cm, the maximum dimension L1 by which the distal edge segments 42a are spaced from each other is in a range of 1.30 to 10.80 cm, preferably 2.50 to 10.80 cm, more preferably 3.75 to 9.90 cm and the maximum dimension L1 by which the distal edge segments 42b are spaced from each other is in a range of 0.05 to 2.25 cm, preferably 0.20 to 1.80 cm. In the case of the article 20 for adult, the minimum transverse dimension L3 of the core 30 extending in the crotch region 22 is in a range of about 12 to about 25 cm, the maximum dimension L1 by which the distal edge segments 42a are spaced from each other is in a range of 3.12 to 30.00 cm, preferably 6.00 to 30.00 cm, more preferably 9.00 to 27.50 cm and the maximum dimension L2 by which the distal edge segments 42b are spaced from each other is in a range of 0.12 to 6.25 cm, preferably 0.48 to 5.00 cm.

Figure 10:
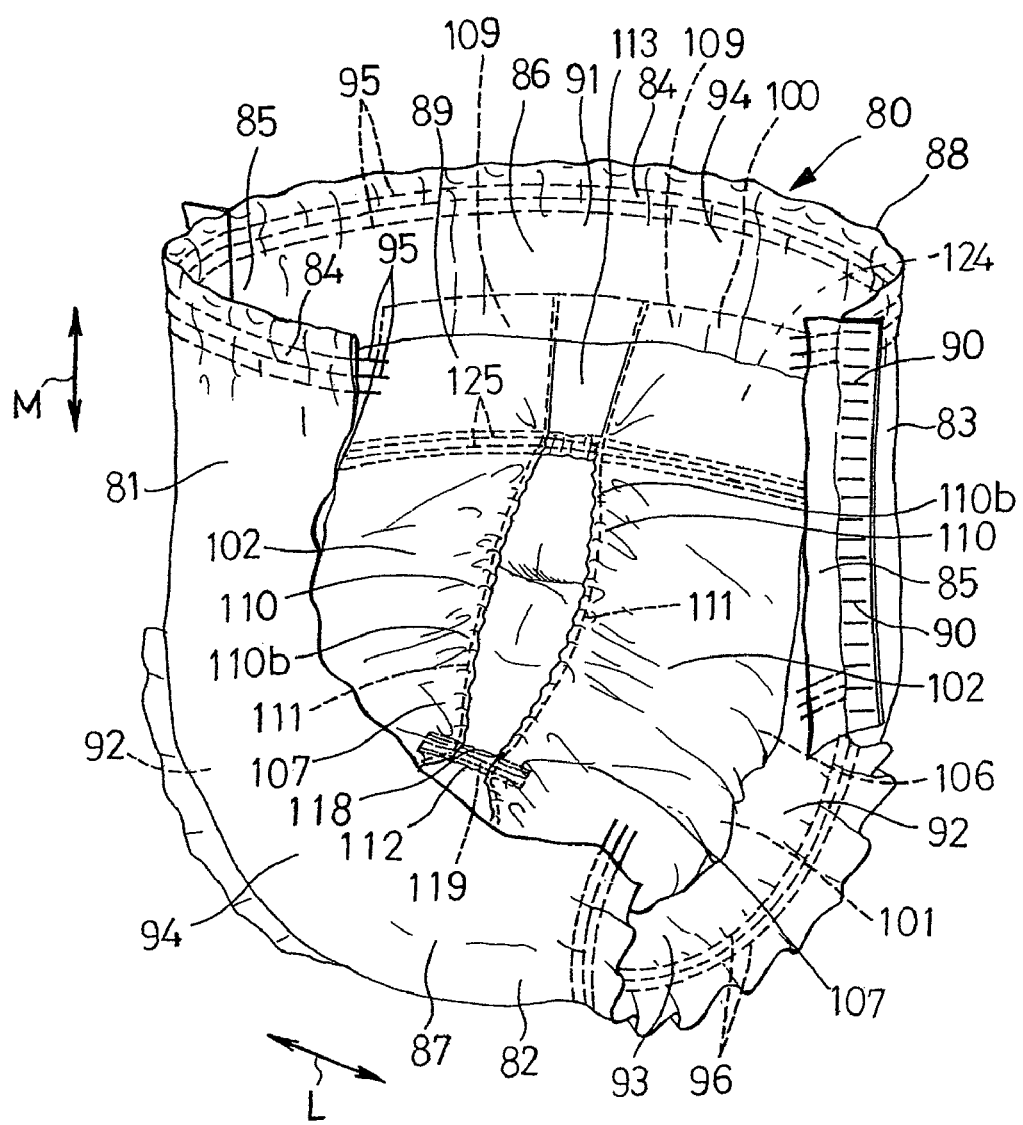
FIG. 10 is a partially cutaway perspective view showing a wearing article according to a second embodiment of the invention as viewed from the front of the article.
Figure 11:
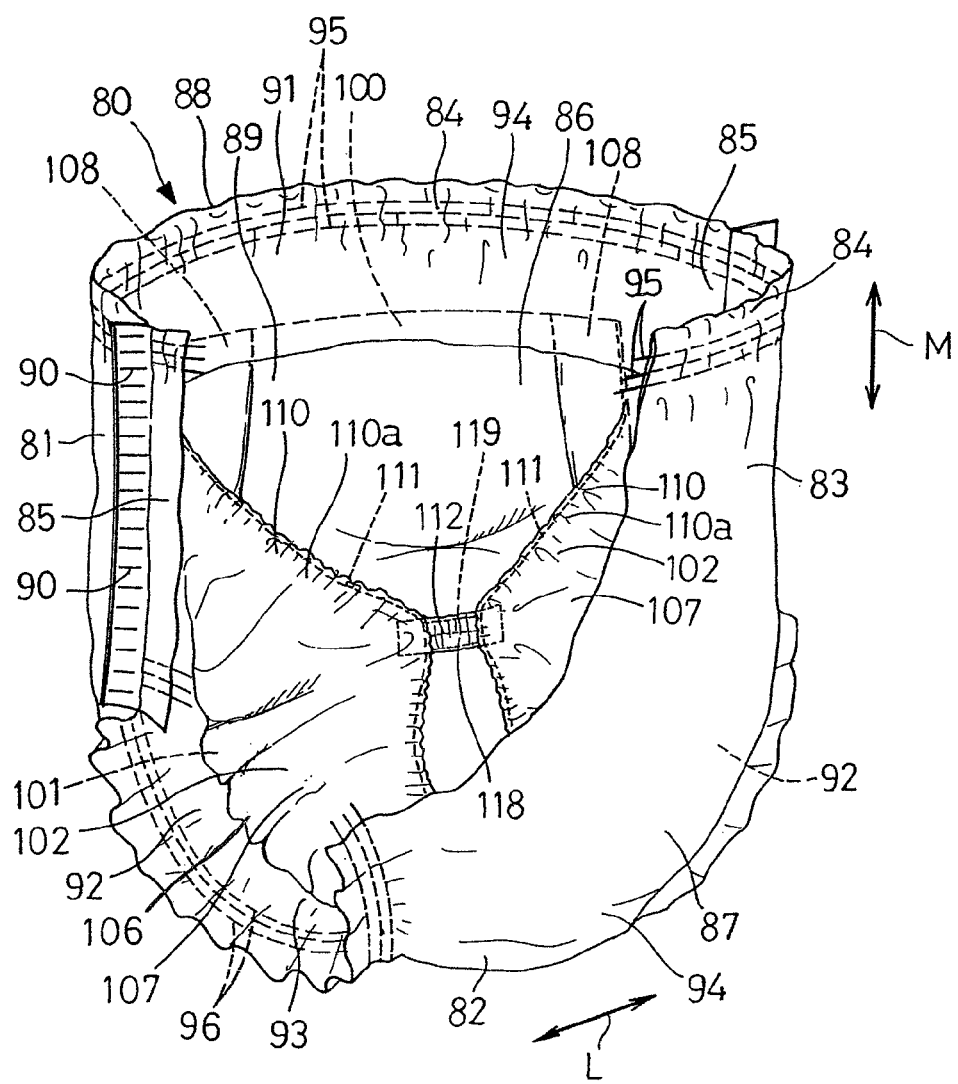
FIG. 11 is a partially cutaway perspective view showing the wearing article according the second embodiment of the invention as viewed from the back of the article.
Figure 12:
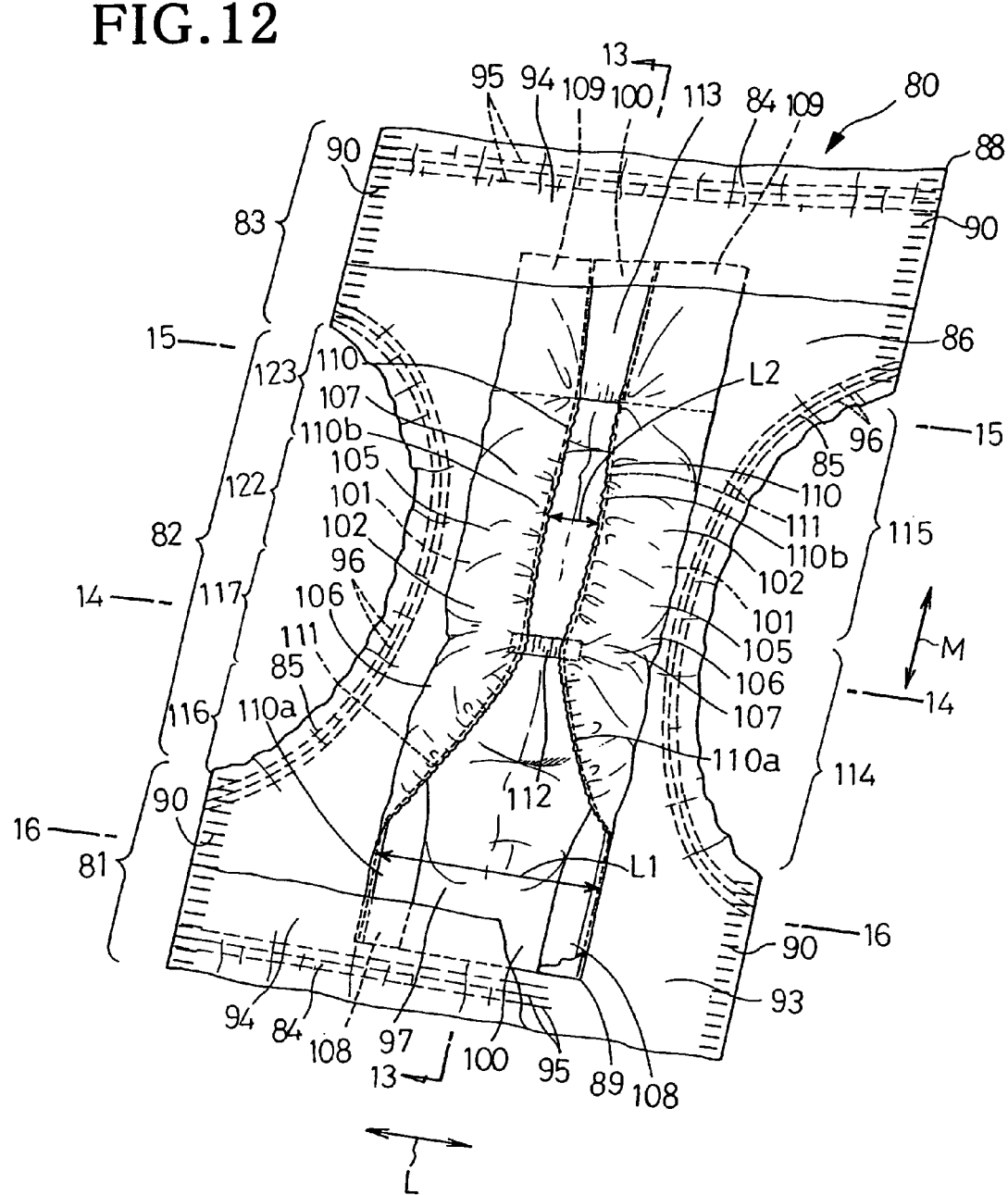
FIG. 12 is a developed perspective view showing the article of FIG. 10.

FIGS. 10 and 11 are partially cutaway perspective views showing a wearing article 80 according to a second embodiment of the invention. FIG. 10 shows the article 80 as viewed from the side of a front waist region 81 and FIG. 11 shows the article 80 as viewed from the side of a rear waist region 83. FIG. 12 is a developed perspective view showing the article 80 of FIG. 10 having the front and rear waist regions 81, 83 disconnected from each other. In FIGS. 10, 11 and 12, a transverse direction is indicated by an arrow L and a longitudinal direction is indicated by an arrow M.

The article 80 has a front waist region 81, a rear waist region 83 and a crotch region 82 extending between these waist regions 81, 83. The article 80 is contoured by transversely extending front and rear ends 84 and margins 85 longitudinally extending side between the front and rear ends 84. The article 80 has a body-side surface 86 destined to come in contact with the wearer's body and a garment-side surface 87 destined to face away from the wearer's body. The article 80 comprises a liquid-impervious first backsheet 88 defining a whole shape including the front and rear waist regions 81, 83 and the crotch region 82, and an absorbent panel 89 attached to the inner surface of the backsheet 88. The margins 85 in the crotch region 82 describe circular arcs which are convex inward in the transverse direction. Thus, the article 80 has a generally hourglass planar shape as will be apparent from FIG. 12. In the article 80, the front and rear waist regions 81, 83 are overlapped and bonded together along the margins 85 at a plurality of heat-sealing lines 90 arranged intermittently along these margins 85. This article 80 is of pants-type having the front and rear waist regions 81, 83 previously connected with each other so as to form a waist-hole 91 and a pair of leg-holes 92 as will be apparent from FIGS. 10 and 11.

As stock material for the backsheet 88, a composite nonwoven fabric composed of two hydrophobic fibrous nonwoven fabric layers 93, 94 laminated together. A plurality of waist elastic members 95 extending in the transverse direction are contractibly attached to the longitudinally ends 84, respectively. The waist elastic members 95 are sandwiched between the nonwoven fabric layers 93, 94, stretched at a predetermined ratio in the transverse direction and bonded to these nonwoven fabric layers 93, 94. A plurality of leg elastic members 96 extending in the longitudinal direction are contractibly attached to the side margins 85, respectively. The leg elastic members 96 are sandwiched between the nonwoven fabric layers 93, 94, stretched in a predetermined ratio in the longitudinal direction and bonded to these nonwoven fabric layers 93, 94.

Figure 13:
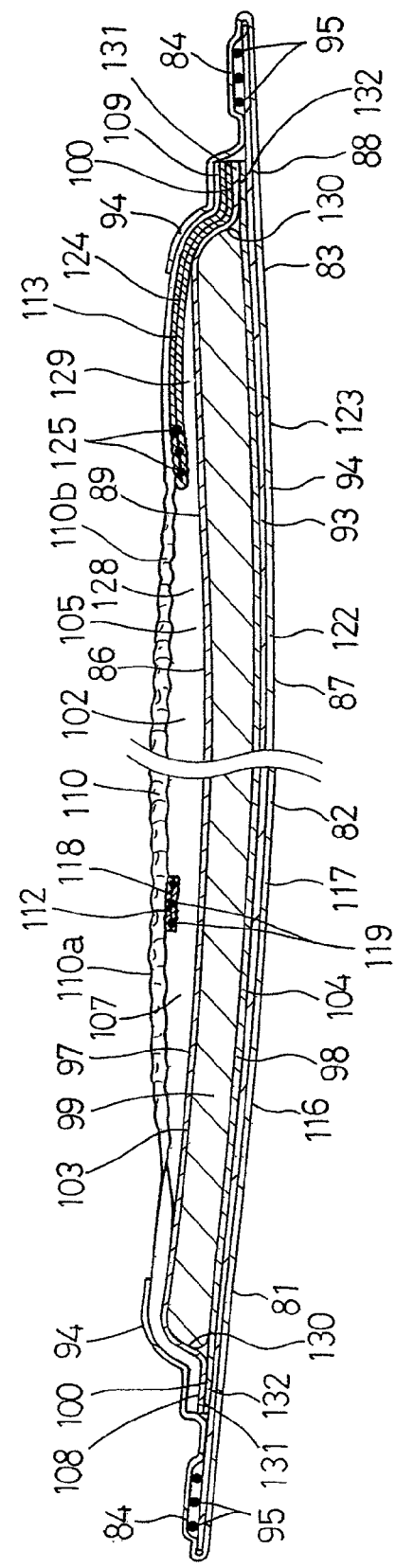
FIG. 13 is a sectional view taken along the line 13-13 in FIG. 12 with a crotch region partially cutaway.

The absorbent panel 89 comprises a liquid-pervious topsheet 97 lying on the body-side, a liquid-impervious second backsheet 98 lying on the garment-side and a liquid-absorbent core 99 sandwiched between the top- and backsheets 97, 98 (i.e., between the body-side surface 86 and the garment-side surface 87) so as to extend over the front and rear waist regions 81, 83 as well as the crotch region 82 (See FIG. 13). The absorbent panel 89 has a substantially rectangular planar shape and occupies the crotch region 82 and parts of the front and rear waist regions 81, 83. The absorbent panel 89 has a pair of transversely extending ends 100 extending in the front and rear waist regions 81, 83 and longitudinally extending margins 101 in coincidence with the margins 85. In the absorbent panel 89, the outer surface of the second backsheet 98 constituting the absorbent panel 89 is secured to the inner surface of the first backsheet 88. A pair of liquid leak-barrier sheets 102 spaced from and opposed to each other in the transverse direction and extending between the front and rear waist regions 81, 83 are attached to the margins 101 (in coincidence with the margins 85 of the article 80).

As stock material for the topsheet 97, a hydrophilic fibrous nonwoven fabric 103 is used. As stock material for the backsheet 98, a breathable liquid-impervious oriented plastic film 104 which contains therein fine particles of inorganic substance such as silica or alumina is used. The core 99 comprises the same mixture as the core 30 of the article 20 in the first embodiment of the invention and entirely wrapped with tissue paper (not shown). The core 99 is bonded to the inner surfaces of the top- and backsheets 97, 98, respectively, by an intermediary of the tissue paper. In the article 80, the inner of the backsheet 88, the outer surfaces of the topsheet 97 and the outer surfaces of the respective leak-barrier sheets 102 define the body-side surface 86 while the outer surface of the backsheet 88 defines the garment-side surface 87.

As stock material for the leak-barrier sheets 102, a hydrophobic fibrous nonwoven fabric 105 is used. Each of the leak-barrier sheets 102 comprises a proximal zone 106 lying on each of the margins 101 and extending in the longitudinal direction, an elasticized distal zone 107 extending in the longitudinal direction and normally biased to rise up above the topsheet 97, and fixed front and rear ends 108, 109 lying-on longitudinal ends of the distal zone 107. Elastic members 111 extending in the longitudinal direction are contractibly attached to distal edges 110 of the respective distal zones 107. More specifically, these elastic members 111 are stretched at a predetermined ratio in the longitudinal direction and bonded in such a stretched state to the distal edges 110 of the respective distal zones 107. The fixed front end 108 is directed outward in the transverse direction of the article 80 while the fixed rear end 109 is directed inward in the transverse direction of the article 80. The leak-barrier sheets 102 are provided with an elongate first band 112 and a rectangular second band 113 both contractibly attached to the leak-barrier sheets 102 and serving to pull the distal zones 107 closer to each other. In the leak-barrier sheets 102, the elastic members 111 contract as the article 80 bows with the body-side surface 86 inside and thereby cause the distal zones 107 to rise up above the outer surface (i.e., the body-side surface 86 of the article 80) of the topsheet 97. In this way, the distal zones 107 form barriers preventing urine and/or feces from moving sideways. Base points at which the distal zones 107 rise up are defined on the core 99 immediately inside transverse side edges 133 of the core 99 as will be described later.

The first band 112 is interposed between the distal zones 107 of the respective leak-barrier sheets 102 spaced from and opposed to each other and extends in the transverse direction. A location of this first band 112 may be strictly defined as follows: Assumed that a longitudinal dimension of the crotch region 82 is bisected into a front half 114 placed aside toward the front waist region 81 and a rear half 115 placed aside toward the rear waist region 83, the first band 112 lies in the front half 114. More strictly, assumed that a longitudinal dimension of the front half 114 is bisected into a first front half 116 placed aside toward the front waist region 81 and a second front half 117 placed aside toward the rear half 115, the first band 112 lies in this second front half 117. In other words, on the assumption that the longitudinal dimension of the crotch region 82 is divided equally into four zones comprising a first zone (corresponding to the first front half 116) through a fourth zone (corresponding to a second rear half 123 as will be described later) arranged from the side of the front waist region 81 toward the rear waist region 83, the first band 112 lies in the second zone (corresponding to the second front half 117).

The first band 112 comprises a hydrophobic or hydrophilic fibrous nonwoven fabric 118 and a plurality of elastic members 119 contractibly attached to this nonwoven fabric 112. The elastic members 119 extend in the transverse direction between the distal zones 107 opposed to each other. The elastic members 119 are stretched at a predetermined ratio in the transverse direction and bonded in such a stretched state to the nonwoven fabric 118. Therefore, the first band 112 is elastically stretchable and contractible in the transverse direction. The first band 112 has fixed opposite ends 120 bonded to the respective distal zones 107 in the vicinity of the distal edges 110 thereof and intermediate segment 121 extending between the fixed opposite ends 120 and left free from the topsheet 97 as well as from the leak-barrier sheets 102 (See FIG. 14). The fixed opposite ends 120 are bonded to the respective distal zones 102 while the first band 112 is stretched at a predetermined ratio in the transverse direction.

The second band 113 extends between the distal zones 107 opposed to each other and further extends between the fixed rear ends 109 opposed to each other, of the respective leak-barrier sheets 102. More strictly, assumed that a longitudinal dimension of the rear half 115 of the crotch region 82 is bisected into a first rear half 122 placed aside toward the front half 114 and a second rear half 123 placed aside toward the rear waist region 83, the second band 113 lies in this second rear half 123. In other words, on the assumption that the longitudinal dimension of the crotch region 82 is divided equally into four zones comprising the first zone (corresponding to the first front half 116) through the fourth zone (corresponding to the second rear half 123) arranged from the side of the front waist region 81 toward the side of the rear waist region 83, the second band 113 lies in the fourth zone.

The second band 113 comprises a hydrophobic or hydrophilic fibrous nonwoven fabric 124 and a plurality of elastic members 125 (shown in FIGS. 10 and 13) contractibly attached to the nonwoven fabric 124. The elastic members 125 extend in the transverse direction between the distal zones 107 opposed to each other. The elastic members 125 are stretched at a predetermined ratio in the transverse direction and bonded in such a stretched state to the nonwoven fabric 124. Therefore, the zone of this second band 113 defined between the distal zones 107 is elastically stretchable and contractible in the transverse direction. The second band 113 has fixed transversely ends 126 bonded to the respective proximal zones 106 as well as to the respective distal zones 107 of the leak-barrier sheets 102 and intermediate segment 127 extending between the fixed transverse ends 126 and left free from the topsheet 97 as well as from the leak-barrier sheets 102. The fixed transverse ends 126 are bonded to the respective distal zones 107 while the second band 113 is stretched at a predetermined ratio in the transverse direction. A zone of the second band 113 extending between the respective fixed rear ends 109 is bonded to the outer surface of the top sheet 97 and to the inner surfaces of the respective leak-barrier sheets 102. As best seen in FIG. 13, the elastic members 125 in this particular embodiment are sandwiched between two layers of the nonwoven fabric 124. The two layers of the nonwoven fabric 124 are also shown in the cross-sectional view of FIG. 15 in which the elastic members 125 are not visible.

Distal edge segments 110a of the respective distal zones 107 extending forward from the first band 112 in the longitudinal direction are spaced from each other in the transverse direction by a dimension which is gradually enlarged from the side of the first band 112 toward the side of the front waist region 81. Distal edge segments 110b of the respective distal zones 107 extending rearward from the first band 112 in the longitudinal direction are spaced from each other in the transverse direction by a predetermined dimension and extend substantially in parallel to each other from the first band 112 toward the rear waist region 83.

Figure 14:
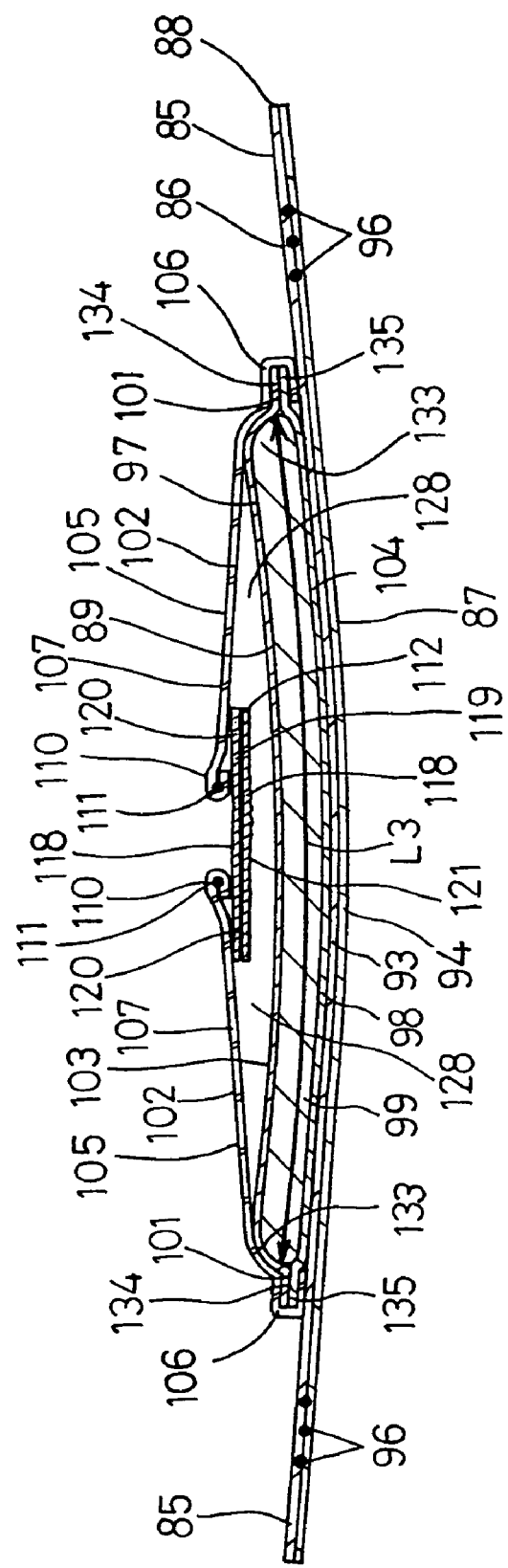
FIG. 14 is a sectional view taken along the line 14-14 in FIG. 12.
Figure 15:
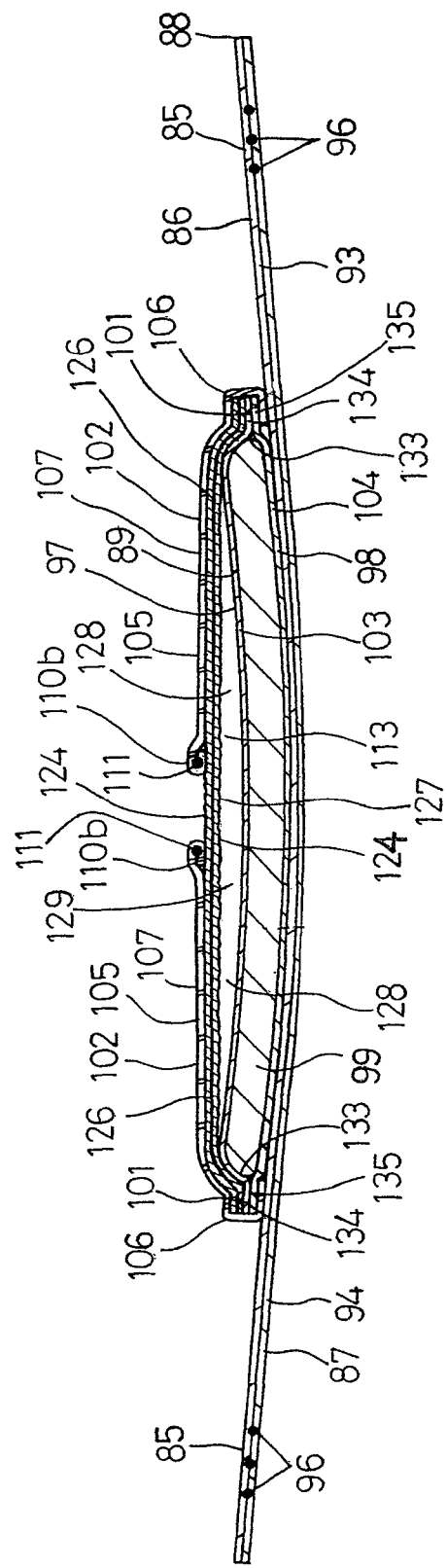
FIG. 15 is a sectional view taken along the line 15-15 in FIG. 12.
Figure 16:
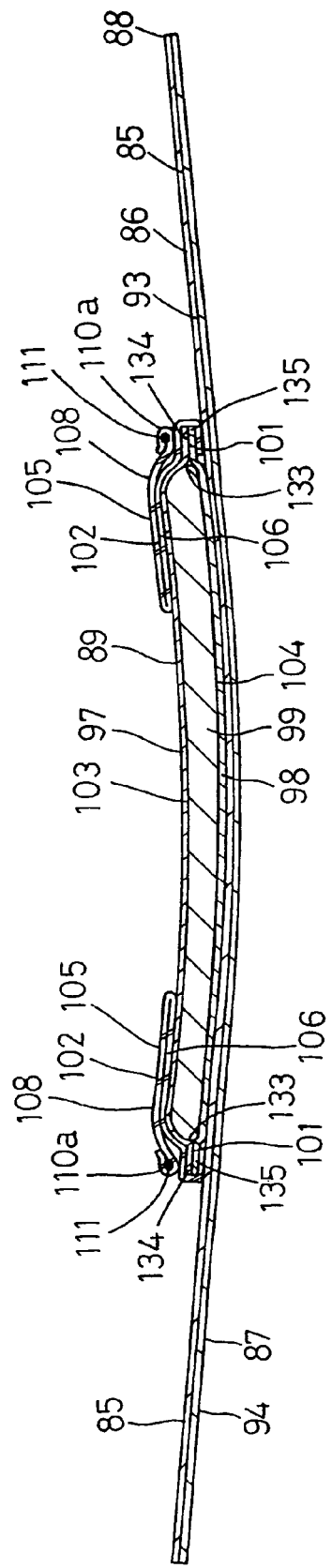
FIG. 16 is a sectional view taken along the line 16-16 in FIG. 12.

FIGS. 13 and 14 are sectional views taken along lines 13-13 and 14-14 in FIG. 12, respectively, wherein the crotch region 82 is partially cutaway. FIGS. 15 and 16 are sectional views taken along lines 15-15 and 16-16 in FIG. 12. Feces receiving space 128 is formed between the distal zones 107 of the respective leak-barrier sheets 102 extending rearward from the first band 112 in the longitudinal direction and the topsheet 97. Between the topsheet 97 and the second band 113, a pocket 129 is formed, which opens from the rear waist region 83 toward a middle of the crotch region 82 as viewed in the longitudinal direction.

The transversely extending ends 100 of the panel 89 respectively comprise respective ends 131, 132 of the top- and backsheets 97, 98 extending outward from transversely extending ends 130 of the core 99 and the longitudinally ends 108, 109 of the respective leak-barrier sheets 102. Along the respective ends 100, the ends 131, 132 of the top- and backsheets 97, 98 are overlapped together and have respective inner surfaces bonded together. To the ends 100, the nonwoven fabric 94 folded back along the ends 84 are bonded. The fixed front ends 108 of the respective leak-barrier sheets 102 are laid along the end 100 of the panel 89 (corresponding to the front waist region 81 of the article 80) and bonded to the respective proximal zones 106 in transversely outward directed state. The fixed rear ends 109 of the respective leak-barrier sheets 102 are laid along the end 100 of the panel 89 (corresponding to the rear waist region 83 of the article 80) and bonded to the second band 113 in transversely inward directed state.

The margins 101 of the panel 89 respectively comprise respective side margins 134, 135 of the top- and backsheets 97, 98 extending transversely outward from side edges 133 of the core 99 and the fixed proximal zones 106 of the respective leak-barrier sheets 102. Along these margins 101, the side margins 134, 135 of the top- and backsheets 97, 98, respectively, are overlapped together with the proximal zones 106 of the respective leak-barrier sheets 102 and the top- and backsheets 97, 98 have the respective inner surfaces bonded to each other. In addition, the outer surface of the topsheet 97 is bonded to the inner surfaces of the respective leak-barrier sheets 102. Sections of the proximal zones 106 of the respective leak-barrier sheets 102 extending transversely outward beyond the respective margins 101 of the panel 89 are folded back transversely inward along the respective margins 101, interposed between the first backsheet 88 and the second backsheet 98 and bonded to the outer and inner surfaces of these sheets 88, 98, respectively.

To put the article 80 on the wearer's body, the wearer's legs are guided through the waist-hole 91, then through the leg-holes 92 and the article 80 is pulled up along the wearer's waist. Similarly to the case of FIGS. 8 and 9 illustrating the positions of the distal edge segments 42*a*, 42*b*, the distal edge segments 100*b* of the distal zones 107 of the respective leak-barrier sheets 102 extending rearward from the first band 112 come close to or in contact with the wearer's inguinal region and further extend into the wearer's buttock cleavage so as to come close to or in contact with both sides of the anus. With the article 80 put on the wearer's body, feces discharged therein is received through a clearance defined between the distal edge segments 100*b* of the respective distal zones 107 into the feces receiving space 128 and the pocket 129. Feces received in this manner are covered from above with the distal zones 107 of the leak-barrier sheets 102 and the intermediate segment 127 of the second band 113. Urine discharged into a space defined between the distal edge segments 100*a* of the respective distal zones 107 is absorbed and contained by the core 99 after permeation through the topsheet 97.

With the article 80 put on the wearer's body, the segments of the distal zones 107 of the respective leak-barrier sheets 102 extending rearward from the first band 112 cooperate with the intermediate segment 127 of the second band 113 to cover feces reliably from above so that feces may be confined within the feces receiving space 128 and the pocket 129. Therefore it is not apprehended that feces once received into the feces receiving space 128 and the pocket 129 might be exposed between the distal zones 107 and come in contact with the wearer's crotch region and/or buttock. Consequentially, the wearer's crotch region and buttock are protected against any amount of feces possibly clinging thereto and thus the wearer's skin is protected against soil with feces. The article 80 allows the distal zones 107 of the respective leak-barrier sheets 102 to prevent urine as well as feces from moving sideways and thereby to prevent urine as well as feces from leaking beyond the side margins 101. At the same time, movement of feces in the longitudinal direction is intercepted by the intermediate segment 127 of the second band 113 and there is no anxiety that any amount of feces discharged in the article 80 might leak from the rear waist region 83.

In the article 80, the first and second bands 112, 113 both having an elasticity in the transverse direction are contractibly attached to the distal zones 107 of the respective leak-barrier sheets 102. Even if movement of the article wearer biases the distal zones 107 of the leak-barrier sheets 102 to move in the transverse direction, a contractile force of the first and second bands 112, 113 functions to hold the distal edge segments 100*b* of the distal zones 107 around the transverse middle of the crotch region 82 and thereby to restrain movement of the distal zones 107. With the article 80 put on the wearer's body, it is thus ensured that the segments of the distal zones 107 of the respective leak-barrier sheets 102 extending rearward in the longitudinal direction from the first band 112 do not significantly shift away from the predetermined positions. In other words, the distal edge segments 100*b* of the distal zones 107 are maintained close to or in contact with the inguinal region as well as both sides of the anus of the wearer. In this way, it is ensured that feces discharged in the article 80 is reliably received by the feces receiving space 128 and the pocket 129 through the clearance defined between the distal edge segments 100*b* of the distal zones 107.

With the article 80 put on the wearer's body, even if the first backsheet 88 is distorted due to movement of the wearer transmitted to this first backsheet 88, it is not apprehended that the distal zones 107 might significantly move. This is for the reason that the core 99 has a stiffness higher than stiffness of the backsheet 88 and the base points from which the distal zones 107 rise up are defined inside the transverse side edges 133 of the core 99. With the article 80 put on the wearer's body, there is no anxiety that the segments of the distal zones 107 extending rearward in the longitudinal direction from the first band 112 might significantly move and the dimension by which the distal edge segments 100*b* of the distal zones 107 are spaced from each other might significantly change. Therefore it is ensured that feces discharged in the article 80 pass through the clearance defined between the distal edge segments 100*b* of the respective distal zones 107 and is received by the feces receiving space 128 and the pocket 129.

In the article 80, the maximum dimension L1 by which the distal edge segments 110*a* of the respective distal zones 107 are spaced from each other is larger than the maximum dimension L2 by which the distal edge segments 100*b* of the distal zones 107 are spaced from each other. An area of the outer surface (i.e., body-side surface 86) of the topsheet 98 exposed between the upper edge segments 110*a* is correspondingly larger than an area of the outer surface (i.e., body-side surface 86) of the topsheet 98 exposed between the upper edge segments 100*b*. More specifically, the maximum dimension L1 by which the distal edge segments 100*a* are spaced from each other is in a range of 26 to 120%, preferably 50 to 120%, more preferably 75 to 110% of the minimum transverse dimension L3 between the side edges 133 of the core 99 extending in the crotch region 82. If the maximum dimension L1 by which the distal edge segments 100a are spaced from each other is less than 26% of the minimum transverse dimension L3 of the core 30, the dimension by which the distal edge segments 110a are spaced from each other will be insufficient and discharge of urine may occur outside the respective distal zones 107.

In the article 80, the maximum dimension L2 by which the distal edge segments 100b of the respective distal zones 107 is in a range of 1 to 25%, preferably 4 to 20% of the minimum transverse dimension L3 between the side edges 133 of the core 99. If the maximum dimension L2 by which the distal edge segments 100b are spaced from each other exceeds 25% of the minimum transverse dimension L3 of the core 99, it may be impossible for the distal zones 107 to cover feces effectively from above. Consequentially feces may be exposed between the distal zones 107 and the wearer's skin may be contaminated over a large area including the crotch region and the buttock with feces clinging thereto. If the maximum dimension L2 by which the distal edge segments 100b are spaced from each other is less than 1% of the minimum transverse dimension L3 of the core 99, it may be difficult for feces to pass through the clearance defined between the distal edge segments 100b and discharge of feces may occur outside the distal zones 107.

So far as the article 80 for baby is concerned, the minimum transverse dimension L3 of the core 99 extending in the crotch region 82 is in a range of about 5 cm to about 9 cm, the maximum dimension L1 by which the upper edge segments 110a are spaced from each other is in a range of 1.30 to 10.80 cm, preferably 2.50 to 10.80 cm, more preferably 3.75 to 9.90 cm and the maximum dimension L2 by which the distal edge segments 100b are spaced from each other is in a range of 0.05 to 2.25 cm, preferably 0.20 to 1.8 cm. In the case of the article 80 for adult, the minimum transverse dimension L3 of the core 99 extending in the crotch region 82 is in a range of about 12 cm to about 25 cm, the maximum dimension L1 by which the distal edge segments 100a are spaced from each other is in a range of 3.12 to 30.00 cm, preferably 6.00 to 30.00 cm, more preferably 9.00 to 27.50 cm and the maximum dimension L2 by which the distal edge segments 100b are spaced from each other is in a range of 0.12 to 6.25 cm, preferably 0.48 to 5.00 cm.

Figure 17:
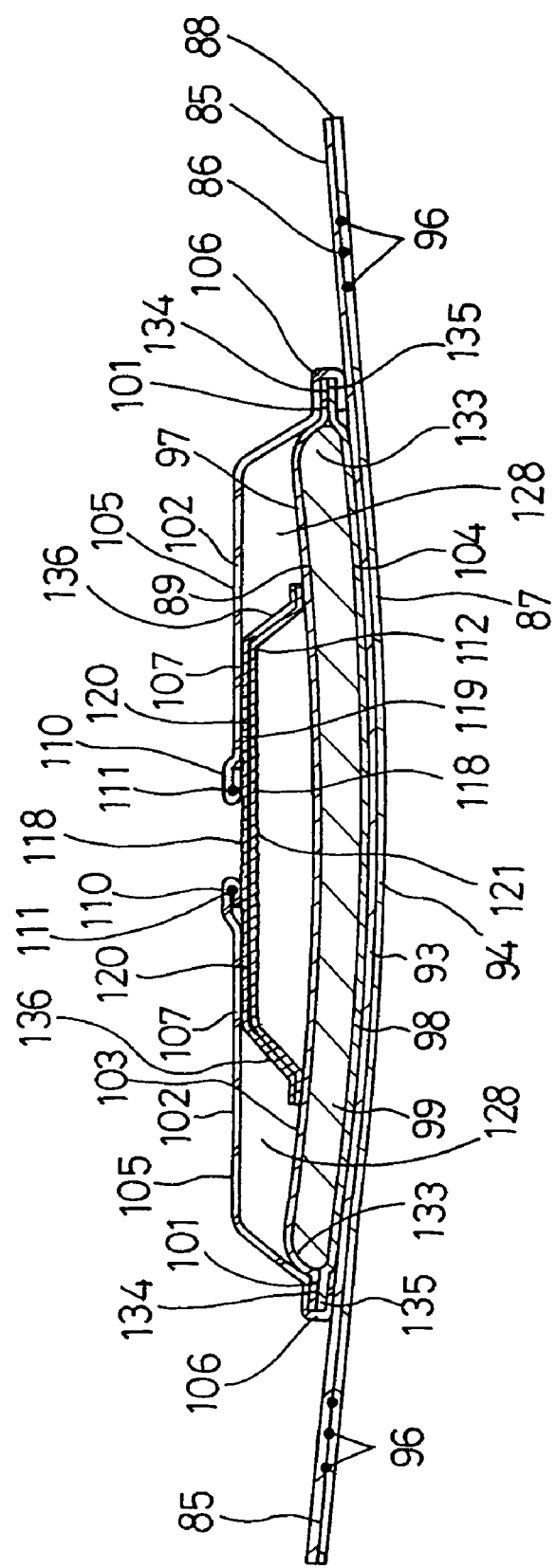
FIG. 17 is a sectional view similar to FIG. 14 showing a first band according to an alternative embodiment.

FIG. 17 is a sectional view similar to FIG. 14 showing the first band 112 according to an alternative embodiment. The first band 112 has a pair of legs 136 extending transversely outward from the fixed opposite ends 120. These legs 136 extend in the feces receiving space 128 from the distal zones 107 to the outer surface of the topsheet 97. The legs 136 are mostly left free from the topsheet 97 as well as from the leak-barrier sheets 102, except that lower ends of legs 136 are bonded to the outer surface of the topsheet 97. With the article 80 according to the embodiment as shown in FIG. 17, even if feces discharged in the article 80 tends to move forward from the first band 112 in the longitudinal direction, these legs 136 of the first band 112 effectively intercept and restrain such movement of feces in the longitudinal direction.

As stock material for the topsheet 28, 97, not only the hydrophilic fibrous nonwoven fabric but also a hydrophobic fibrous nonwoven fabric having a plurality of apertures may be used. As stock material for the backsheet 29, 88, 98 and the leak-barrier sheets 33, 102, a breathable liquid-impervious plastic film or a composite sheet consisting of a breathable liquid-impervious plastic film and a hydrophobic fibrous nonwoven fabric laminated together also may be used. In addition, a composite nonwoven fabric (e.g., SM nonwoven fabric, SMS nonwoven fabric) consisting of a melt blown fibrous nonwoven fabric having high water-resistance laminated on at least one surface of a spun bond fibrous nonwoven fabric having a high strength as well as a good flexibility. As stock material for the first and second bands 44, 45, 112, 113, an elastic fibrous nonwoven fabric made of elastic fibers obtained by melt spinning thermoplastic elastomer resin may be used. It is also possible to use a composite nonwoven fabric consisting of a hydrophilic fibrous nonwoven fabric made of crimped fibers laminated on at least one surface of an elastic fibrous nonwoven fabric as stock material for these bands 44, 45, 112, 113.

The fibrous nonwoven fabric may be selected from the group consisting of a spun lace nonwoven fabric, a needle punch nonwoven fabric, a melt blown nonwoven fabric, a thermal bond nonwoven fabric, a spun bond nonwoven fabric and a chemical bond nonwoven fabric. The hydrophilic fibrous nonwoven fabric may be made of any one of synthetic fibers modified to become hydrophilic, semi-synthetic fibers and regenerated fibers, or composite fibers consisting of a mixture thereof. The hydrophobic fibrous nonwoven fabric may contain therein water repellent treated semi-synthetic fibers or regenerated fibers. While not specified, the synthetic fibers may be selected from the group consisting of polyester-, polyacrylonitrile-, polyvinylchloride-, polyethylene-, polypropylene- and polystyrene-based synthetic fibers. It is also possible to use, as synthetic fibers, core-sheath-type composite fibers, parallel-type composite fibers, modified macaroni fibers, micro-porous fibers or conjugative type composite fibers.

Bonding of the sheets 28, 29, 33, 88, 97, 98, 102 one to another, bonding of the cores 30, 99 to the sheets 28, 29, 97, 98, bonding of the elastic members 31, 32, 51, 58, 95, 96, 119, 125 to the sheets 33, 102 and the nonwoven fabric layers 34, 35, 50, 56, 93, 94, 118, 124, and bonding of the bands 44, 45, 112, 113 to the sheets 28, 33, 97, 102 may be carried out using adhesive. The sheets 28, 29, 33, 88, 97, 98, 102 and the nonwoven fabric layers 34, 35, 50, 56, 93, 94, 118, 124 are coated with adhesive preferably in the pattern such as spiral, wavy, zigzag, dotted or striped pattern. By coating the sheets 28, 29, 33, 88, 97, 98, 102 and the nonwoven fabric layers 34, 35, 50, 56, 93, 94, 118, 124 with adhesive in such pattern, these sheets 28, 29, 33, 88, 97, 98, 102 are intermittently bonded one to another, the cores 30, 99 are intermittently bonded to the sheets 28, 29, 97, 98, and the elastic members 31, 32, 51, 58, 95, 96, 119, 125 are intermittently bonded to the sheets 33, 102 and the nonwoven fabric layers 34, 35, 50, 56, 93, 94, 118, 124. Adhesive may be selected from a group consisting of hot melt adhesive, acrylic adhesive and rubber-based adhesive.

The entire discloses of Japanese Patent Application No. 2004-370105 filed on Dec. 21, 2004 including specification, drawings and abstract are herein incorporated by reference in its entirety.

What is claimed is:

1. A disposable wearing article, comprising:
a front waist region;
a rear waist region;
a crotch region extending in a longitudinal direction of said article between said waist regions;
longitudinally opposite front and rear ends extending in a transverse direction of the article;
a pair of transversely opposite side edges extending in the longitudinal direction;
opposite body-side and garment-side surfaces;
a pair of leak-barrier sheets laid on the body-side surface in at least said crotch region among said front and rear waist regions and said crotch region, said leak-barrier sheets comprising (a) proximal zones lying along said side edges of said article so as to extend in said longitudinal direction of said article, (b) elasticized distal zones extending in the longitudinal direction and normally biased to rise up above said body-side surface, and (c) fixed front and rear ends which lie on longitudinal ends of said distal zones and are directed in said transverse direction of said article;

a first band which has opposite end portions directly attached to said distal zones of said leak-barrier sheets and extends between said distal zones to pull said distal zones toward each other in the transverse direction, said first band being located in said crotch region toward said front waist region; and a second band rearwardly spaced in the longitudinal direction from the first band and directly attached to the distal zones of said leak-barrier sheets so as to extend between said distal zones and to pull said distal zones toward each other in the transverse direction;

wherein the fixed front ends of said leak-barrier sheets are directed outward in the transverse direction and bonded to the body-side surface in such a directed state, and the fixed rear ends of said leak-barrier sheets are directed inward in the transverse direction and bonded to the body-side surface in such a directed state, so that (i) a first distance, by which first distal edge segments of said distal zones extending forward in the longitudinal direction from said first band are spaced in the transverse direction from each other, gradually increases from said first band toward said front waist region, and (ii) a second distance, by which second distal edge segments of said distal zones extending rearward in the longitudinal direction from said first band are spaced in the transverse direction from each other, gradually decreases from said first band toward said rear waist region;

said first band further has, between said end portions, a middle portion spanning between the distal zones of said leak-barrier sheets and free of direct attachment to the body-side surface of said crotch region;

said first band is entirely spaced upward from the body-side surface as said distal zones rise up above said body-side surface;

the spacing between the first band and the body-side surface allows body discharges to move, in use, along the body-side surface and underneath the first band from a rear half of the crotch region to a front half thereof; and the rear half of said crotch region includes a first rear half positioned toward said front half and a second rear half positioned toward said rear waist region, and a front end of said second band is located in said second rear half of the crotch region.

2. The wearing article as defined by claim 1, wherein the front half of said crotch region includes a first front half positioned toward said front waist region and a second front half positioned toward said rear half, and said first band is located in said second front half of the crotch region.

3. The wearing article as defined by claim 2, wherein said first band extends transversely of the crotch region without obstructing, in use, movement of body discharges along the body-side surface in the longitudinal direction from the rear half of said crotch region to the front waist region.

4. The wearing article as defined by claim 1, further comprising a liquid-absorbent core adapted for absorption and containment of bodily fluids sandwiched between the body-side surface and the garment-side surface at least in said crotch region among said front and rear waist regions and said crotch region, the maximum dimension of the first distance is in a range of 26 to 120% of a minimum transverse dimension of said core extending in said crotch region, and the maximum dimension of the second distance is in a range of 1 to 25% of the minimum transverse dimension of said core extending in said crotch region.

5. The wearing article as defined by claim 4, wherein said second band further comprises:

a rear portion which, in a region rearward of said core and along said rear end of said article, is sandwiched between (i) the fixed rear ends of the leak-barrier sheets and (ii) a liquid-pervious topsheet defining the body-side surface of the article; and a front portion which includes the front end of said second band, spans the second distance between the second distal edge segments of said distal zones and defines, together with the distal zones of the leak-barrier sheets, a top wall of a pocket opening forwardly for receiving fecal material in use.

6. The wearing article as defined by claim 5, wherein said second band extends in the transverse direction without obstructing, in use, movement of body discharges along the body-side surface in the longitudinal direction from said crotch region to the front waist region, and further comprises elastic members contractible in the transverse direction and directly attached along said front end of the second band.

7. The wearing article as defined by claim 6, wherein the front portion of the second band further defines a rear wall of the pocket, the distal zones of the barrier sheets define side walls of the pocket, and the body-side surface defines a bottom of the pocket; and the front portion of the second band is adapted to cover, from above, fecal material received in the pocket.

8. The wearing article as defined by claim 6, wherein said second band extends forwardly in the longitudinal direction from the rear portion located in the rear waist region into the crotch region and terminates at the front end of the second band in the second rear half of the crotch region, without extending into the first rear half of said crotch region.

9. The wearing article as defined by claim 6, wherein said first band is elastically stretchable and contractible in the transverse direction and is attached to the distal zones of said leak-barrier sheets when said first band is being stretched in the transverse direction so that said distal zones are pulled towards each other in the transverse direction by the so-bonded first band.

10. The wearing article as defined by claim 9, wherein the front end of said second band is elastically stretchable and contractible in the transverse direction due to the elastic members, and is attached to the distal zones of said leak-barrier sheets when the front end of said second band, together with the elastic members attached thereto, is being stretched in the transverse direction so that said distal zones are pulled towards each other in the transverse direction by the so-bonded second band when the elastic members contract.

11. The wearing article as defined by claim 1, wherein said first band is elastically stretchable and contractible in the transverse direction and is attached to the distal zones of said leak-barrier sheets when said first band is being stretched in the transverse direction so that said distal zones are pulled towards each other in the transverse direction by the so-bonded first band.

12. The wearing article as defined by claim 11, wherein the front end of said second band is elastically stretchable and contractible in the transverse direction and is attached to the distal zones of said leak-barrier sheets when the front end of said second band is being stretched in the transverse direction so that said distal zones are pulled towards each other in the transverse direction by the so-bonded second band.

13. The wearing article as defined by claim 1, wherein said first band is entirely free of direct attachment to said body-side surface.

14. The wearing article as defined by claim 1, wherein said first band is directly attached to a remainder of said article only via the direct attachment of the end portions of said first band to the distal zones of said leak-barrier sheets.

\* \* \* \* \*